US009567104B2

(12) United States Patent
Sweers et al.

(10) Patent No.: US 9,567,104 B2
(45) Date of Patent: *Feb. 14, 2017

(54) UTILIZATION OF AIRCRAFT BONDLINE EMBEDDED CURRENT SENSORS IN THE DETERMINATION OF A LIGHTNING DAMAGE INDEX

(71) Applicant: THE BOEING COMPANY, Chicago, IL (US)

(72) Inventors: Gregory J. Sweers, Chicago, IL (US); Carol E. Anway, Chicago, IL (US); Andrew M. Robb, Chicago, IL (US); Jeong-Beom Ihn, Chicago, IL (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,152

(22) Filed: Nov. 20, 2015

(65) Prior Publication Data
US 2016/0077027 A1 Mar. 17, 2016

Related U.S. Application Data

(63) Continuation-in-part of application No. 14/337,095, filed on Jul. 21, 2014, now Pat. No. 9,267,906, which
(Continued)

(51) Int. Cl.
G01B 7/00 (2006.01)
B64D 45/00 (2006.01)
(Continued)

(52) U.S. Cl.
CPC ............ B64D 45/00 (2013.01); B29C 65/483 (2013.01); B29C 65/5021 (2013.01);
(Continued)

(58) Field of Classification Search
CPC .. G01M 99/00; G01M 5/0033; G01M 5/0016; G01M 5/0091
See application file for complete search history.

(56) References Cited

U.S. PATENT DOCUMENTS 3,906,308 A 9/1975 Amason et al.
5,417,385 A 5/1995 Arnold et al.
(Continued)

FOREIGN PATENT DOCUMENTS

EP 0573350 12/1993
EP 0573778 12/1993
(Continued)

OTHER PUBLICATIONS

PCT International Search Report and Written Opinion, Application No. PCT/US2012/024425 (which is counterpart PCT application for U.S. Appl. No. 14/337,095), May 10, 2012.
(Continued)

Primary Examiner — Elias Desta
(74) Attorney, Agent, or Firm — Vista IP Law Group LLP; Cynthia A. Dixon

(57) ABSTRACT

Systems, methods, and apparatus for using aircraft bondline embedded current sensors to determine a lightning damage index are disclosed. A method of predicting lightning strike damage to at least one type of aircraft involves sensing, with at least one current sensor node embedded in at least one type of aircraft, induced current. The method further involves generating, with at least one current sensor node, at least one current signal representative of the induced current. Also, the method involves determining, electromagnetic density data associated with at least one region of at least one type of aircraft by using at least one current signal. Further, the method involves creating an index that provides a numeric representation for predicted lightning strike damage to at least one type of aircraft based on the electromag-
(Continued)

netic density data, dimensions of at least one type of aircraft, and design features of at least one type of aircraft.

18 Claims, 22 Drawing Sheets

Related U.S. Application Data is a continuation-in-part of application No. 13/085,450, filed on Apr. 12, 2011, now Pat. No. 8,812,251, application No. 14/948,152, which is a continuation-in-part of application No. 13/327,608, filed on Dec. 15, 2011, now Pat. No. 9,217,811.

(51) Int. Cl.

| | |
|---|---|
| *B29C 65/48* | (2006.01) |
| *B29C 65/50* | (2006.01) |
| *B29C 65/82* | (2006.01) |
| *B29C 65/00* | (2006.01) |
| *B64C 3/20* | (2006.01) |
| *G01N 27/02* | (2006.01) |
| *G01N 27/20* | (2006.01) |
| *G01M 5/00* | (2006.01) |
| *B29L 31/30* | (2006.01) |
| *B29K 105/20* | (2006.01) |
| *F16B 11/00* | (2006.01) |
| *B64C 1/00* | (2006.01) |

(52) U.S. Cl.
CPC ...... *B29C 65/5028* (2013.01); *B29C 65/5057* (2013.01); *B29C 65/8276* (2013.01); *B29C 65/8284* (2013.01); *B29C 66/1122* (2013.01); *B29C 66/45* (2013.01); *B29C 66/721* (2013.01); *B64C 3/20* (2013.01); *G01M 5/0033* (2013.01); *G01M 5/0083* (2013.01); *G01M 5/0091* (2013.01); *G01N 27/025* (2013.01); *G01N 27/026* (2013.01); *G01N 27/20* (2013.01); *B29C 65/4835* (2013.01); *B29C 65/8292* (2013.01); *B29C 66/71* (2013.01); *B29C 66/7212* (2013.01); *B29C 66/72141* (2013.01); *B29C 66/72143* (2013.01); *B29C 66/7392* (2013.01); *B29C 66/7394* (2013.01); *B29C 66/73921* (2013.01); *B29C 66/73941* (2013.01); *B29K 2105/206* (2013.01); *B29L 2031/3076* (2013.01); *B29L 2031/3079* (2013.01); *B29L 2031/3082* (2013.01); *B29L 2031/3085* (2013.01); *B64C 2001/0072* (2013.01); *B64D 2045/0085* (2013.01); *F16B 11/006* (2013.01); *Y02T 50/433* (2013.01)

(56) References Cited

U.S. PATENT DOCUMENTS

| | | | |
|---|---|---|---|
| 6,384,610 | B1 | 5/2002 | Wilson |
| 6,859,757 | B2 * | 2/2005 | Muehl ............... G06Q 10/06 235/375 |
| 7,367,236 | B2 | 5/2008 | Georgeson et al. |
| 7,414,416 | B2 | 8/2008 | Watkins, Jr. et al. |
| 7,867,621 | B2 * | 1/2011 | Rawlings ............ B32B 15/08 428/425.9 |
| 8,159,369 | B1 | 4/2012 | Koenigs et al. |
| 8,264,215 | B1 | 9/2012 | Kovach et al. |
| 9,217,811 | B1 * | 12/2015 | Sweers ............... G01W 1/16 |
| 2007/0166831 | A1 | 7/2007 | Watkins, Jr. et al. |
| 2009/0294022 | A1 | 12/2009 | Hayes et al. |
| 2010/0005896 | A1 | 1/2010 | Miller et al. |
| 2011/0049292 | A1 | 3/2011 | Kruckenberg et al. |

FOREIGN PATENT DOCUMENTS

| | | |
|---|---|---|
| EP | 2070688 | 6/2009 |
| WO | 0046593 | 8/2000 |
| WO | 03076953 | 9/2003 |

OTHER PUBLICATIONS

O'Loughlin, Report No. DOT/FAA/AR-04/13, "General Aviation Lightning Strike Report and Protection Level Study", Aug. 2004.
Gough, "The Prediction and Occurrences of Aircraft Lightning Encounters at Amsterdam-Schiphol Airport", 47th AIAA Aerospace Science Meeting Including the New Horizons Forum and Aerospace Exposition Jan. 5-8, 2009, Orlando, Florida.

\* cited by examiner

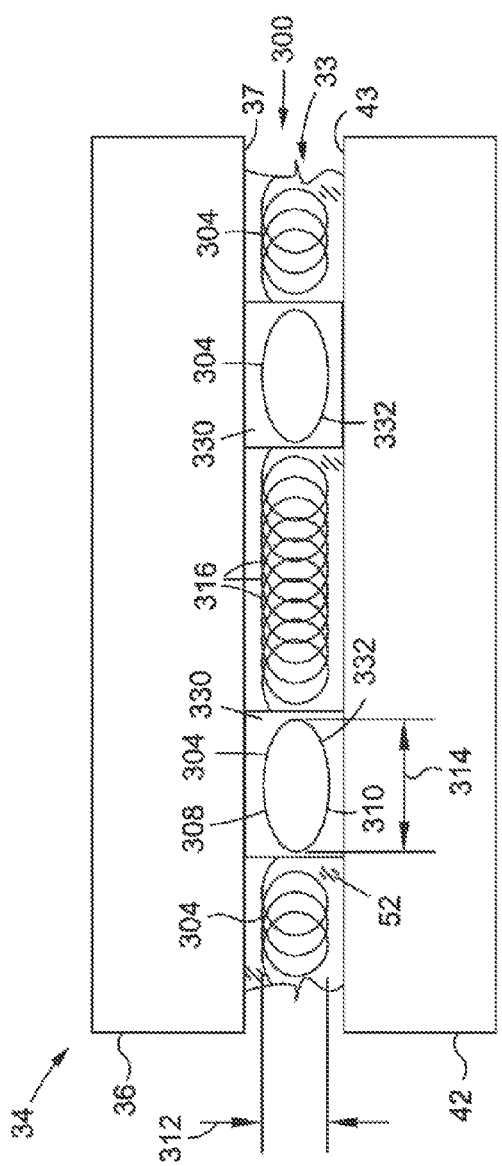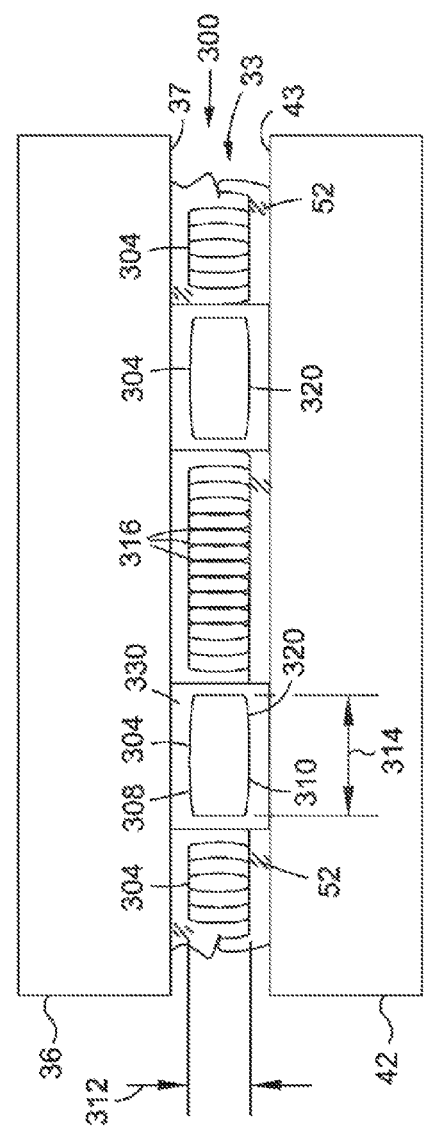

| Airplane Type | Nose to Wing Root Angle | Winglet | Radome Design (*curve ratio, material, supplemental protection) | Electromagnetic Density, nose (kV/m) | Lightning strike probability, initial attach to nose | Flight Altitude (ft)/Change in strike probability | +Geographic Operating Area/strike probability | #Storm Seasonal effect on strike probability |
|---|---|---|---|---|---|---|---|---|
| Single engine turboprop | 75° | No | High curve, Metallic, No | 150 | 40 | 8000/15%<br>10000/20%<br>12000/30% | 2% | None |
| Short haul regional jet, monoplane, jet engine | 30° | No | Med curve, Non-metallic, Yes | 250 | 60 | 8000/15%<br>10000/20%<br>12000/30% | 5% | Increase 20% |
| Short haul single-aisle jet airliner, twin engine | 30° | No | Low curve, Non-metallic, Yes | 200 | 50 | 8000/15%<br>10000/20%<br>12000/30% | 5% | Increase 20% |
| Narrow body business jet | 45° | No | Med curve, Non-metallic, Yes | 220 | 55 | 8000/15%<br>10000/20%<br>12000/30% | 2% | Increase 20% |
| Narrow body business jet | 45° | Yes | Med curve, Non-metallic, Yes | 220 | 45 | 8000/15%<br>10000/20%<br>12000/30% | 10% | None |
| Long haul twin aisle, jet airliner, body, twin engine | 45° | No | Low curve, Non-metallic, Yes | 190 | 55 | 8000/15%<br>10000/20%<br>12000/30% | 5% | None |
| Long haul, twin aisle, jet airliner, twin engine | 45° | Yes | Low curve, Non-metallic, Yes | 190 | 45 | 8000/15%<br>10000/20%<br>12000/30% | 2% | Increase 20% |

⌒ Thunderstorm days in the US range from 10 to 100 per year in this model. +Thunderstorm days = 0-20, rating is Low and strike probability is 2%
+Thunderstorm days = 20-80, rating is Med and strike probability is 5%
+Thunderstorm days = 80-100, rating is High and strike probability is 10%
Storm Season = Yes, increase strike probability by 20%
Storm Season = No, no change in strike probability

* Curve W/H ≈ 1 = Low
* Curve W/H ≈ 2/3 = Med
* Curve W/H ≈ 1/3 = High

FIG. 17 ations Ser. No. 14/337,095, now U.S. Pat. No. 9,267,906, filed Jul. 21, 2014, entitled "Bondline Embedded Current Sensor"; which is a Continuation-In-Part application of, and claims priority to and the benefit of, U.S. patent application Ser. No. 13/085,450, filed Apr. 12, 2011, entitled "System and Method for Monitoring Bonding Integrity", issued as U.S. Pat. No. 8,812,251. This application is a Continuation-In-Part application of, and claims priority to and the benefit of, U.S. patent application Ser. No. 13/327,608, now U.S. Pat. No. 9,217,811, filed Dec. 15, 2011, entitled "Lightning Damage Index". The contents of all of these applications are hereby incorporated by reference in their entirety.

UTILIZATION OF AIRCRAFT BONDLINE EMBEDDED CURRENT SENSORS IN THE DETERMINATION OF A LIGHTNING DAMAGE INDEX

CROSS-REFERENCE TO RELATED APPLICATIONS

This application is a Continuation-In-Part application of, and claims priority to and the benefit of, U.S. patent appli-

FIELD

The present disclosure relates to aircraft bondline embedded current sensors. In particular, it relates to utilization of aircraft bondline embedded current sensors in the determination of a lightning damage index.

BACKGROUND

It is possible for aircraft to be struck by lightning while airborne and consequently to incur damage from the lightning strike. However, certain types of aircraft may have designs for which a lightning strike results in more extensive repair needs than other aircraft, which in turn may result in decreased operating time for such aircraft. Such outcomes may lead to customer dissatisfaction due to increased repair costs and limited fleet availability. This can raise issues for aircraft manufacturers that have to provide increased product support to address lightning damage. Aside from the type of aircraft, other factors can contribute to lightning strikes and resulting damage, such as flight frequency, flight altitude, time of year for operating, and geographic area of operation. A system (e.g., that employs bondline embedded current sensors) that considers types of aircraft and other contributing factors in predicting lightning strike damage could reduce repair needs and help operators maintain schedules and fleet availability.

SUMMARY

The present disclosure relates to a method, system, and apparatus for a utilization of aircraft bondline embedded current sensors in the determination of a lightning damage index. In one or more embodiments, a method of predicting lightning strike damage to at least one type of aircraft involves sensing, with at least one current sensor node embedded in at least one type of aircraft, induced current. The method further involves generating, with at least one current sensor node, at least one current signal representative of the induced current. Also, the method involves determining, electromagnetic density data associated with at least one region of at least one type of aircraft by using at least one current signal. Further, the method involves creating an index that provides a numeric representation for predicted lightning strike damage to at least one type of aircraft based on the electromagnetic density data, dimensions of at least one type of aircraft, and design features of at least one type of aircraft.

In one or more embodiments, the method further involves passing electrical current, having a magnetic field, through an adhesive layer of a cured bondline embedded in at least one type of aircraft. In at least one embodiment, a current sensor network is embedded in the adhesive layer, and the current sensor network comprises at least one current sensor node. Also, the method involves inducing the induced current in the current sensor network in response to the magnetic field.

In at least one embodiment, the method further involves determining the dimensions of at least one type of aircraft by measuring the dimensions of at least one type of aircraft. Also, the method involves determining the design features of at least one type of aircraft by assessing the design features of at least one type of aircraft.

In one or more embodiments, the index further comprises a numeric representation for predicted lightning strike damage to a specific location on at least one type of aircraft based on the electromagnetic density data, the dimensions of at least one type of aircraft, and the design features of at least one type of aircraft.

In at least one embodiment, the method further involves modifying the numeric representation with at least one factor relating to the respective at least one type of aircraft. In some embodiments, the method further involves assigning a numeric value to at least one factor. In one or more embodiments, the method further involves determining an algorithmic association between the numeric representation with the numeric value of at least one factor. In one or more embodiments, at least one factor comprises a departure frequency of each of at least one type of aircraft. In some embodiments, at least one factor comprises a geographic region in which each of at least one type of aircraft operates.

In at least one embodiment, at least one factor comprises an altitude at which each of at least one type of aircraft operates. In some embodiments, at least one factor further comprises a frequency of a specific altitude within a constant time at which each of at least one type of aircraft operates.

In one or more embodiments, at least one factor comprises a time period during which each of at least one type of aircraft operates. In at least one embodiment, the time period is a specified calendar time period. In some embodiments, the time period is a seasonal time period. In one or more embodiments, the time period is adjustable.

In at least one embodiment, the method further involves determining an impact level associated with at least one type of aircraft, the electromagnetic density data, the dimensions of at least one type of aircraft, the design features of at least one type of aircraft, and/or at least one factor. Also, the method involves modifying the numeric representation and/or at least one factor with the associated impact level. In some embodiments, each impact level is obtained from a table that displays each impact level associated with the respective at least one type of aircraft, the electromagnetic density data, the dimensions of at least one type of aircraft, the design features of at least one type of aircraft, and at least one factor.

In one or more embodiments, a system for predicting lightning strike damage to at least one type of aircraft involves at least one current sensor node, embedded in at least one type of aircraft, to sense induced current, and to generate at least one current signal representative of the induced current. The system further involves at least one computer processor to determine electromagnetic density data associated with at least one region of at least one type of aircraft by using at least one current signal, and to create an index that provides a numeric representation for predicted lightning strike damage to at least one type of aircraft based on the electromagnetic density data, dimensions of at least one type of aircraft, and design features of at least one type of aircraft.

In at least one embodiment, the system further involves an adhesive layer of a cured bondline, embedded in at least one type of aircraft, to pass electrical current through. In one or more embodiments, the electrical current has a magnetic field. In some embodiments, a current sensor network is embedded in the adhesive layer, and the current sensor network comprises at least one current sensor node. In at least one embodiment, the induced current is induced in the current sensor network in response to the magnetic field. In one or more embodiments, the current sensor network further comprises at least one inductive coil.

In an embodiment of the disclosure, there is provided a system for monitoring adhesive integrity within a cured bondline of a bonded structural assembly. The system comprises a bonded structural assembly having a cured bondline. The cured bondline comprises an adhesive layer, a scrim ply layer integrated with the adhesive layer, and an electrical sensor network integrated with the scrim ply layer. The system further comprises an electrical power source for providing electrical power to the electrical sensor network. The system further comprises a digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a system for monitoring adhesive integrity within a cured bondline of a bonded composite lamina assembly. The system comprises a bonded composite lamina assembly having a cured bondline. The cured bondline comprises an adhesive layer, a scrim ply layer integrated with the adhesive layer, and an electrical sensor network integrated with the scrim ply layer. The system further comprises a wireless electrical power source for providing electrical power to the electrical sensor network. The system further comprises a wireless digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a method for monitoring adhesive integrity within a cured bondline of a bonded structural assembly. The method comprises providing a bonded structural assembly having a cured bondline. The cured bondline comprises an adhesive layer, a scrim ply layer integrated with the adhesive layer, and an electrical sensor network integrated with the scrim ply layer. The method further comprises activating the electrical sensor network to monitor adhesive integrity of the cured bondline on demand by interpreting changes in local dynamic responses and electromechanical properties directly measured within the cured bondline. The method further comprises retrieving and processing adhesive integrity data of the cured bondline from the electrical sensor network via a digital data communications network.

Also disclosed is a current detection system for monitoring electrical current passing through a cured bondline bonding a first structure to a second structure of a structural assembly. The structural assembly may be included in an aircraft or in any vehicular or non-vehicular structure. The current detection system may include a current sensor network embedded in an adhesive layer of the cured bondline. The current sensor network may include a plurality of inductive coils and a plurality of current sensor nodes electrically interconnecting the inductive coils to form a plurality of current sensor loops generating induced current in response to a magnetic field associated with an electrical current passing through the adhesive layer. The current sensor nodes may generate current signals representative of the induced current. The current sensor network may include a digital data communications network located external to the cured bondline and receiving the current signals from the current sensor nodes and detecting and monitoring electrical current passing through the cured bondline based on the current signals.

In a further embodiment, disclosed is a method for monitoring electrical current passing through a cured bondline. The method may include passing an electrical current through an adhesive layer of a cured bondline of a structural assembly. The electrical current may have a magnetic field associated therewith. The adhesive layer may contain a current sensor network including a plurality of inductive coils electrically interconnected at a plurality of current sensor nodes and forming a plurality of current sensor loops. The method may include inducing an induced current in the current sensor loops in response to the magnetic field, and generating, at the current sensor nodes, current signals representative of the induced current. The method may additionally include transmitting the current signals to a digital data communications network located external to the cured bondline, and detecting and monitoring the electrical current using the digital data communications network based on the current signals.

In one or more embodiments, the present disclosure teaches a method of predicting lightning strike damage to one or more types of aircraft. The disclosed method involves generating data relating to the one or more types of aircraft by measuring the dimensions of the one or more types of aircraft, assessing the design features of the one or more types of aircraft, and/or obtaining electromagnetic density data associated with regions of the one or more types of aircraft. The method further involves creating an index that provides a numeric representation for predicted lightning strike damage to the one or more types of aircraft based on the generated data.

In one or more embodiments, the index further comprises a numeric representation for predicted lightning strike damage to a specific location on the aircraft based on the generated data. In at least one embodiment, the method further involves modifying the numeric representation with one or more factors relating to the respective one or more types of aircraft. In some embodiments, the method further involves assigning a numeric value to the one or more factors. In one or more embodiments, the method further involves an algorithmic association between the numeric representation with the numeric value of the one or more factors.

In at least one embodiment, the one or more factors comprises a departure frequency of each of the one or more types of aircraft. In some embodiments, the one or more factors comprises a geographic region in which each of the one or more types of aircraft operates. In one or more embodiments, the one or more factors comprises an altitude at which each of the one or more types of aircraft operates. In at least one embodiment, the one or more factors further comprises a frequency of a specific altitude within a constant time at which each of the one or more types of aircraft operates.

In one or more embodiments, the one or more factors comprises a time period during which each of the one or more types of aircraft operates. In at least one embodiment, the time period is a specified calendar time period. In some embodiments, the time period is a seasonal time period. In one or more embodiments, the time period is adjustable.

In at least one embodiment, the method further involves determining an impact level associated with at least one of the one or more types of aircraft, the generated data, and the one or more factors, and modifying at least one of the numeric representation and the one or more factors with the associated impact level. In some embodiments, each impact level is obtained from a table that displays each impact level associated with the respective at least one of the one or more types of aircraft, the generated data, and the one or more factors.

In one or more embodiments, a system for predicting lightning strike damage to one or more types of aircraft involves data generated for each of the one or more types of aircraft comprising dimensions of the one or more types of aircraft, design features of the one or more types of aircraft, and/or electromagnetic density data associated with different areas of the aircraft. In at least one embodiment, the system further involves an index that compiles the data and provides a numeric representation for predicted lightning strike damage to the one or more types of aircraft based on the compilation of the data.

In at least one embodiment, the index further comprises a numeric representation for predicted lightning strike damage to a specific location on the aircraft based on the data. In some embodiments, the system further involves one or more factors that is applied to the numeric representation to modify the numeric representation. In one or more embodiments, each of the one or more factors has a numeric value. In some embodiments, there is an algorithmic association between the numeric representation and the one or more factors. In at least one embodiment, the system further involves one or more impact levels that is associated with at least one of the one or more types of aircraft, the data, and the one or more factors, and that is applied to modify at least one of the numeric representation and the one or more factors.

The features, functions, and advantages that have been discussed can be achieved independently in various embodiments of the disclosure or may be combined in yet other embodiments, further details of which can be seen with reference to the following description and drawings.

DRAWINGS

The disclosure can be better understood with reference to the following detailed description taken in conjunction with the accompanying drawings which illustrate preferred and exemplary embodiments, but which are not necessarily drawn to scale, wherein:

FIG. 14 is an illustration of a partial cross-sectional view of a further embodiment of the current sensor network wherein the inductive coils have a rectangular cross-sectional shape.

FIG. 15 is an illustration of a partial cross-sectional view of another embodiment of the current sensor network wherein the inductive coils have an oval cross-sectional shape.

FIG. 17 shows an example embodiment of an index for predicted lightning strike damage to various types of aircraft.

DESCRIPTION

Figure 1:
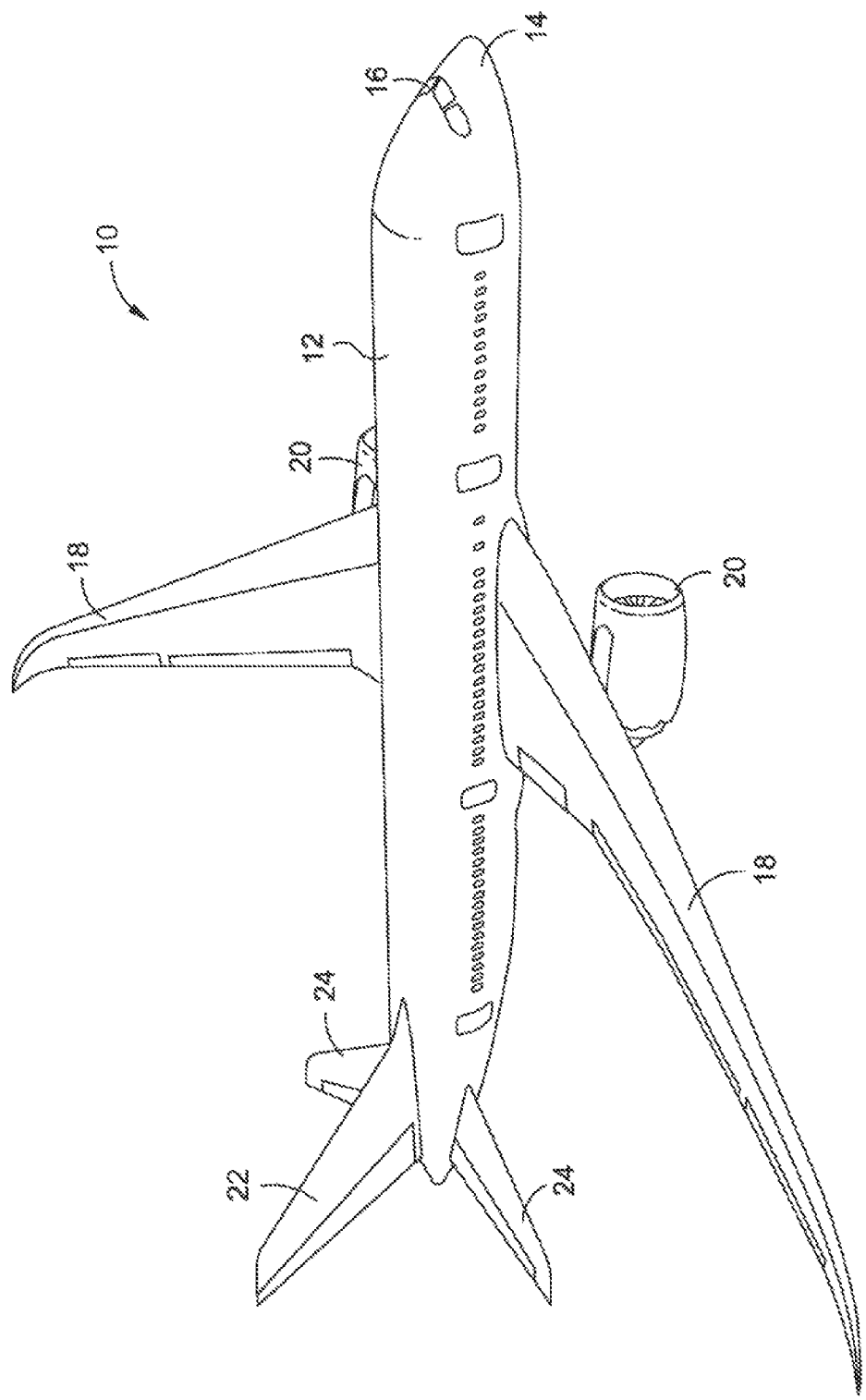
FIG. 1 is an illustration of a perspective view of an exemplary aircraft for which one of the embodiments of the system and method of the disclosure may be used.

The methods and apparatus disclosed herein provide an operative system for utilization of aircraft bondline embedded current sensors in the determination of a lightning damage index. In particular, this system employs the use of sensors, installed onto an aircraft, in identifying electric current passing through a bondline caused by an electromagnetic field associated with a lightning strike within a structure for determining a lightning damage index (LDI). The disclosed system provides a tool that can provide aircraft operators with less down time associated with unexpected lightning strike damage by generating LDI values to be used in a logistics system for repair preparedness. With sensors embedded into the aircraft structure, the sensors can provide real-time data in determining the LDI values.

In one or more embodiments, on the ground during test, sensor data can be used to generate the LDI for a specific region of the aircraft (i.e. to predict the amount of damage a region of the aircraft will suffer due to a lightning strike). In at least one embodiment, during flight, sensor data can be used real time to determine how much intensity a region of the aircraft experienced during a lightning strike (i.e. to predict the amount damage suffered by a region of the aircraft due to a lightning strike).

The methods and apparatus disclosed herein also provide an operative system for a lightning damage index. Specifically, this system employs a lightning damage index that is used to predict the propensity of a lightning strike to an aircraft and the location of the strike in order to assess the potential degree of damage to the aircraft that the lightning strike will cause. The lightning damage index can help aircraft operators to predict potential lightning strike damage in an effort to reduce operational burdens and other losses related to subsequent repairs to the aircraft from lightning strikes.

As previously mentioned above, it is possible for aircraft to be struck by lightning while airborne and consequently to incur damage from the lightning strike. However, certain types of aircraft may have designs for which a lightning strike results in more extensive repair needs than other aircraft, which in turn may result in decreased operating time for such aircraft. Such outcomes may lead to customer dissatisfaction due to increased repair costs and limited fleet availability. This can raise issues for aircraft manufacturers that have to provide increased product support to address lightning damage. Aside from the type of aircraft, other factors can contribute to lightning strikes and resulting damage, such as flight frequency, flight altitude, time of year for operating, and geographic area of operation. A system (e.g., that employs bondline embedded current sensors) that considers types of aircraft and other contributing factors in predicting lightning strike damage could reduce repair needs and help operators maintain schedules and fleet availability.

The disclosed system design provides an index that allows for predicting potential resulting damage from a lightning strike on an aircraft. The system accounts for multiple aircraft designs and data relating to a lightning strike associated with the respective designs. The system also accounts for contributing factors to lightning strikes, such as flight frequency, flight altitude, time of year for operating, and geographic area of operation.

It should be noted that the manufacture and assembly of structures and structural components has increasingly involved the use of bonded joints or bondlines, such as adhesive bonded joints or bondlines, instead of fastener devices, to bond or join the structural components together. Adhesive bonded joints may be used in bonding of composite structural components in combination with other composites or other materials such as metal. In this regard, adhesive bonded composite structures and structural components may typically be used in the manufacture and assembly of aircraft, spacecraft, rotorcraft, watercraft, automobiles, trucks, buses, and other vehicles and structures due to the design flexibility and low weight of such composite structures and structural components.

Known inspection methods and devices exist for assessing the integrity of adhesive bonded joints or bondlines in order to measure the quality, soundness, effectiveness, performance, strength, or other characteristics of the adhesive bond, as well as to assess the ability of the adhesive bond to function reliably as required throughout the predicted lifetime of the bonded structure or structural components. Such known inspection methods and devices may include a variety of time-consuming techniques such as visual inspection, localized non-destructive inspection methods, laser bond and ultrasonic inspection devices, or other known methods and devices. These known inspection methods and devices may require that the hardware be pulled out of service for the inspection and may not have the ability to interrogate the bondline while the component part is in-service. In addition, such inspection methods and devices may increase costs and flow time to the process of assuring bondline integrity. Moreover, such known inspection methods and devices may only be carried out at certain times or on a periodic basis, rather than having the information about the bondline integrity available at all times on demand and available on a continuous, real time basis.

In particular, known visual inspection and localized non-destructive inspection methods and devices may not be effective where visual access to the adhesive bonded joints or bondlines is limited or not possible, for example, if such adhesive bonded joints or bondlines are located in a remote or interior location or beneath the surface. Access to interior bonded joints and bondlines may be difficult or not possible without disassembly or damage to the structures or structural components, such as removing a part or drilling a hole into a structure for insertion of a measurement tool. In addition, ultrasonic inspections may require specialized equipment, substantial operator training, and effective access to the structural component.

In addition, known methods and devices exist for monitoring the health of a composite structure with the use of external sensors. For example, U.S. Patent Publication Number 2007/0166831 A1 to Watkins, Jr. et al., discloses a method for monitoring the health of a composite structure by disposing a condition sensor on the surface of the composite structure. However, positioning sensors on the external surface of the structure may provide measurements of the whole structure including measurements through the structural components and the bondline. Such known methods and devices may provide only indirect and less accurate measurements of bondline characteristics and not direct and more accurate measurements of bondline characteristics at or within the bondline. In addition, alignment and positioning of external sensors may be complicated by accessibility to the structure or structural component, for example, inaccessibility to one side of a composite sandwich structure.

Accordingly, there is a need in the art for an improved system and method for monitoring bonding integrity directly at or within adhesive bonded joints or bondlines of structures or structural assemblies where such improved system and method provide advantages over known systems and methods.

A related aspect of monitoring the integrity of adhesively-bonded joints is with regard to detecting and monitoring high-intensity transient electrical currents that may pass through bonded joints. For example, aircraft must be capable of withstanding high-intensity current due to lightning strikes. In view of the undesirable effects of high-intensity electrical current on adhesive, and considering the increasing use of adhesively-bonded joints in the primary structure of an aircraft, it is becoming necessary to detect and monitor electrical current flow through bonded joints as may occur in the event of a lightning strike. In this regard, it is necessary to understand the distribution of current flow from a lightning strike toward and through bonded joints to facilitate the testing, design, and development of aircraft structures capable of withstanding or avoiding excessively-high current flow through bonded joints. As indicated above, known methods for assessing the integrity of adhesively-bonded joints are limited to time-consuming techniques such as visual inspection, localized non-destructive inspection methods, the use of laser bond and ultrasonic inspection devices, or other known methods and devices.

Accordingly, there exists a need in the art for a system and method for detecting and monitoring electrical current flow through bonded joints so that appropriate lighting protection may be provided to such bonded joints.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Embodiments of the present disclosure may be described herein in terms of functional and/or logical components and various processing steps. It should be appreciated that such components may be realized by any number of hardware, software, and/or firmware components configured to perform the specified functions. For example, an embodiment of the present disclosure may employ various integrated circuit components (e.g., memory elements, digital signal processing elements, logic elements, look-up tables, or the like), which may carry out a variety of functions under the control of one or more processors, microprocessors, or other control devices. In addition, those skilled in the art will appreciate that embodiments of the present disclosure may be practiced in conjunction with other components, and that the system described herein is merely one example embodiment of the present disclosure.

For the sake of brevity, conventional techniques and components related to bondline embedded current sensors, and other functional aspects of the system (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

A. Bondline Embedded Current Sensor

Now referring to the Figures, FIG. 1 is an illustration of a perspective view of an exemplary prior art aircraft 10 for which one of the embodiments of a system 30 (see FIG. 2) or a system 100 (see FIG. 3), or a method 200 (see FIG. 9) for monitoring adhesive integrity may be used. The aircraft 10 comprises a fuselage 12, a nose 14, a cockpit 16, wings 18 operatively coupled to the fuselage 12, one or more propulsion units 20, a tail vertical stabilizer 22, and one or more tail horizontal stabilizers 24. Although the aircraft 10 shown in FIG. 1 is generally representative of a commercial passenger aircraft, the systems 30, 100 and method 200 disclosed herein may also be employed in other types of aircraft. More specifically, the teachings of the disclosed embodiments may be applied to other passenger aircraft, cargo aircraft, military aircraft, rotorcraft, and other types of aircraft or aerial vehicles, as well as aerospace vehicles such as satellites, space launch vehicles, rockets, and other types of aerospace vehicles. It may also be appreciated that embodiments of systems, methods and apparatuses in accordance with the disclosure may be utilized in other vehicles, such as boats and other watercraft, trains, automobiles, trucks, buses, and other types of vehicles.

Figure 2:
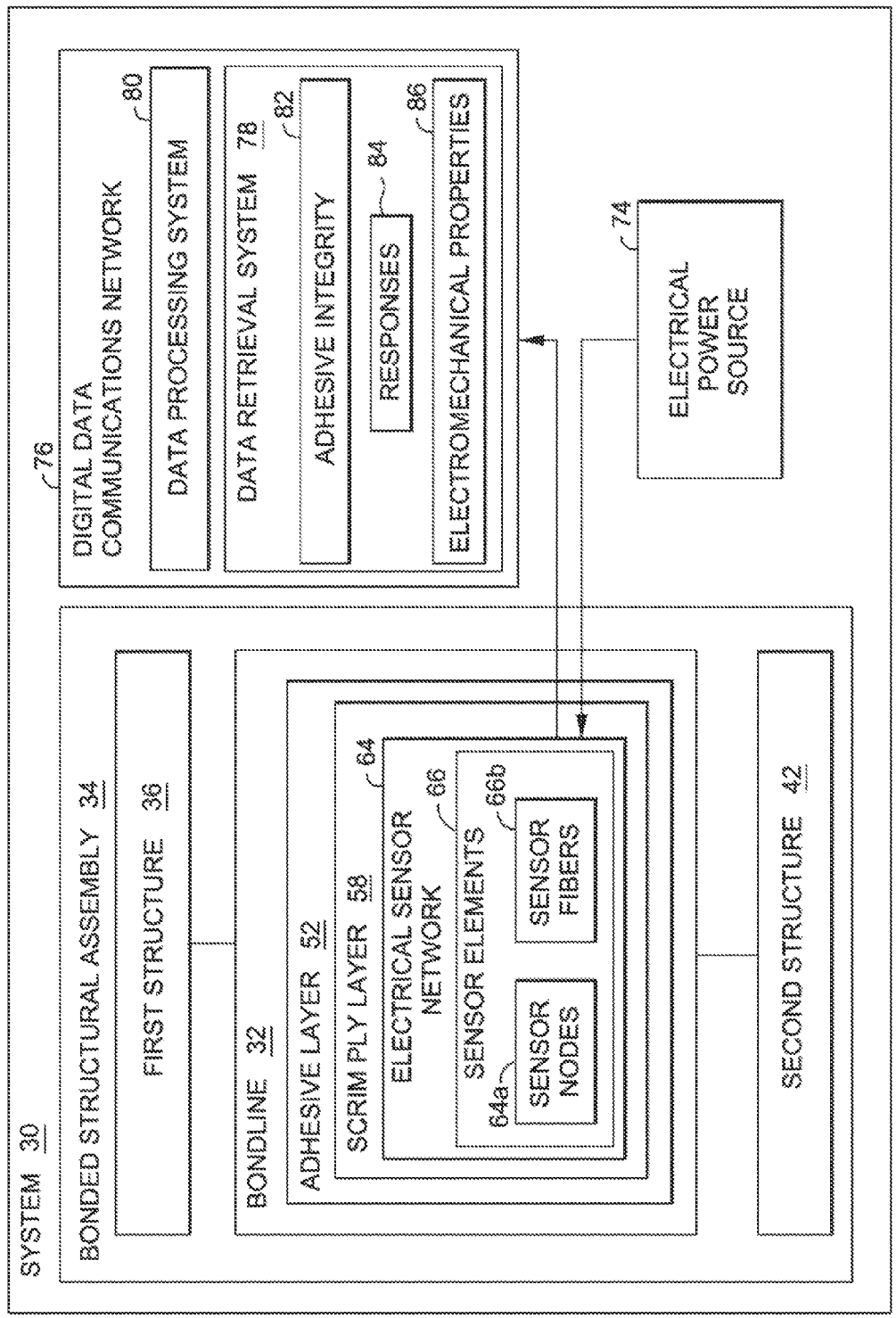
FIG. 2 is an illustration of a block diagram of one of the embodiments of a system for monitoring adhesive integrity of the disclosure.

FIG. 2 is an illustration of a block diagram of one of the embodiments of the system 30 for monitoring adhesive integrity. In one embodiment of the disclosure, there is provided the system 30 for monitoring adhesive integrity within a cured bondline 32 or joint of a bonded structural assembly 34. As used herein, the term "adhesive integrity" means a measure of the quality, soundness, effectiveness, performance, and strength of an adhesive bond and the ability of the adhesive bond to function reliably as required throughout the predicted lifetime of a bonded structural assembly or structure.

Figure 4A:
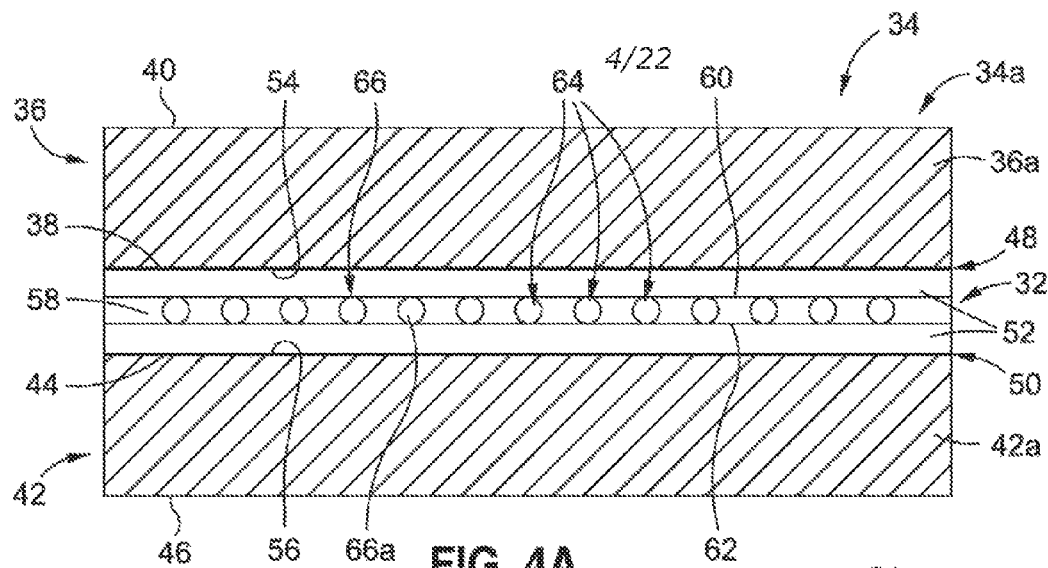
FIG. 4A is an illustration of a partial cross-sectional view of an embodiment of a bonded structure having one of the embodiments of the system of the disclosure.
Figure 4B:
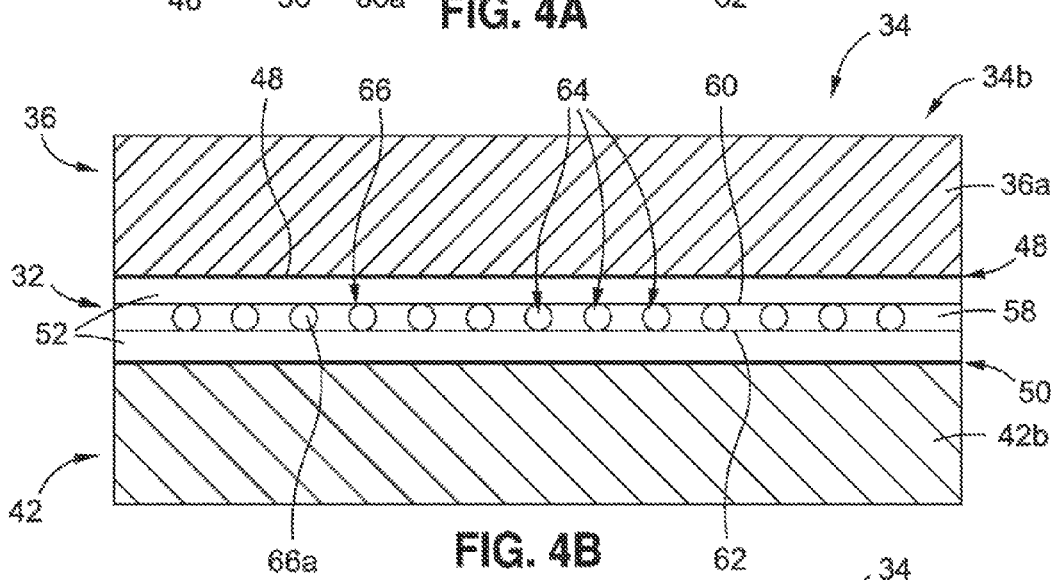
FIG. 4B is an illustration of a partial cross-sectional view of another embodiment of a bonded structure having one of the embodiments of the system of the disclosure.
Figure 4C:
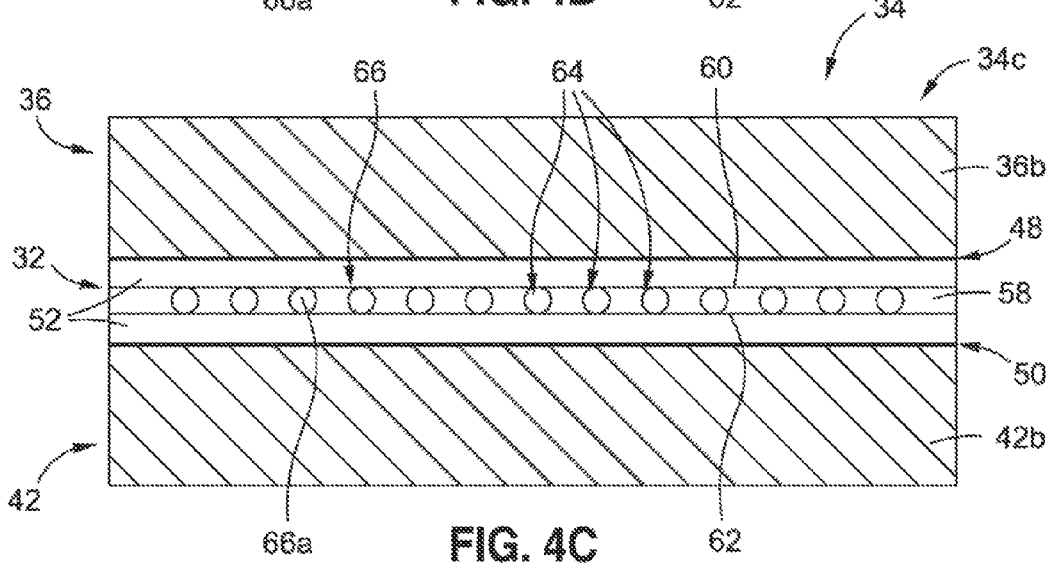
FIG. 4C is an illustration of a partial cross-sectional view of another embodiment of a bonded structure having one of the embodiments of the system of the disclosure.

The system 30 comprises the bonded structural assembly 34 having the cured bondline 32 or joint. As shown in FIGS. 4A-4C, the bonded structural assembly 34 may comprise a first structure 36 and a second structure 42. The first structure 36 has a first side 38 and a second side 40. The second structure 42 has a first side 44 and a second side 46. The first structure 36 may be made of a composite material, a metal material, a combination of a composite material and a metal material, or another suitable material. The second structure 36 may be made of a composite material, a metal material, a combination of a composite material and a metal material, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Exemplary composite material may typically comprise a reinforcement fiber, such as reinforcement fabric, dispersed in a thermoplastic or thermoset polymer matrix. Reinforcement fabrics may comprise fibers made of metallic, carbon, glass, boron, ceramic, and polymeric fibers. The reinforcement fibers may be in woven or non-woven mats, or they may be dispersed in the matrix. Matrix material may comprise thermoplastic materials such as polyamides, polyolefins and fluoropolymers, and thermosets such as epoxies and polyesters. Preferably, the metal material for the first structure 36 and/or the second structure 42 comprises aluminum, stainless steel, titanium, alloys thereof, or another suitable metal or metal alloy.

FIG. 4A is an illustration of a partial cross-sectional view of an embodiment of a bonded structure 34*a* having a first structure 36*a* made of one material, such as a metal, and having a second structure 42*a* made of the same material, such as a metal, as the material of the first structure 36*a*. FIG. 4B is an illustration of a partial cross-sectional view of another embodiment of a bonded structure 34*b* having the first structure 36*a* made of one material, such as a metal, and having a second structure 42*b* made of a different material, such as a composite, than the material of the first structure 36*a*. FIG. 4C is an illustration of a partial cross-sectional view of another embodiment of a bonded structure 34*c* having a first structure 36*b* made of one material, such as a composite, and having the second structure 42*b* made of the same material, such as a composite, as the material of the first structure 36*b*.

As shown in FIGS. 4A-4C, the cured bondline 32 or joint of the bonded structural assembly 34 comprises an adhesive layer or layers 52. As shown in FIG. 4A, the adhesive layer 52 has a first side 54 and a second side 56. The adhesive layer or layers 52 may comprise an adhesive material such as an epoxy adhesive, a polyurethane adhesive, a toughened acrylic adhesive, or another suitable adhesive. Epoxy adhesives generally have good strength, low shrinkage, and produce strong durable bonds with most materials. Polyurethane adhesives generally are fast curing, provide strong resilient joints which are impact resistant, and have good low temperature strength. Toughened acrylic adhesives generally are fast curing, have high strength and toughness, and bond well to a variety of materials.

As shown in FIG. 2, the cured bondline 32 further comprises a scrim ply layer 58 integrated with the adhesive layer or layers 52 (see also FIGS. 4A-4C and 5A-5B). As shown in FIG. 4A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is preferably multifunctional and acts as an adhesive layer by being integrated in the adhesive layers 52 and also acts as a bondline monitoring system.

As shown in FIGS. 4A-4C, the cured bondline 32 further comprises an electrical sensor network 64 integrated with the scrim ply layer 58. The electrical sensor network 64 preferably comprises a plurality of spaced sensor elements 66. The sensor elements 66 may comprise active sensor nodes 66*a* (see FIG. 6), active sensor fibers 66*b* (see FIG. 7), active sensor wires (not shown), sensor fiber optic wires (not shown), sensor coatings on fibers (not shown), carbon nanotubes (not shown), passive sensors, or another suitable sensor element. The sensor elements 66 may be comprised of a matrix of high-resistivity, insulative thermoplastic or thermoset polymer and conductive fillers, such as carbon black, carbon nanotubes, and metallic particles, such as silver, nickel and aluminum, although other conductive and semi-conductive particles such as metallic oxides may be used. The sensor elements 66 may also comprise electrode sensors, piezoelectric sensors, pulse-echo (PE) sensors, pitch-catch active sensors, through transmission (TT) sensors, shear wave sensors, resonance sensors, mechanical impedance sensors, lamb wave sensors, rayleigh wave sensors, stoneley wave sensors, or other suitable sensors. Preferably, the sensor elements 66 are active sensors. However, passive sensors may also be used. Active sensors may generate electric current or voltage directly in response to environmental stimulation. Passive sensors may produce a change in some passive electrical quantity, such as capacitance, resistance, or inductance, as a result of stimulation and typically may require additional electrical energy for excitation. Some RFID devices may be active and some RFID devices may be passive.

The sensor elements 66 may be removable and placed manually on the scrim ply layer 58 integrated with the adhesive layer 52 and later removed. Alternatively, the sensor elements 66 may be bonded or otherwise attached to or within the scrim ply layer 58 by an adhesive or one or more mechanical fasteners (not shown). The sensor elements 66 may be small discrete sensors in the form of strips or electrodes covering some or substantially all of the surface portions of the scrim ply layer 58 or in the form of mats, fibers or woven sheets attached to or on the scrim ply layer 58.

The system 30 integrates the sensing of the cured bondline 32 into the bonded structural assembly 34 and provides a method to interrogate the characteristics and integrity of the cured bondline 32 on demand or continuously. The smart adhesive layer 52 and the scrim ply layer 58 may be a permanent part of the bonded structural assembly 34. The monitoring system 30 provides for an internal electrical sensor network 64 and internal sensor elements 66 at or within the cured bondline 32 to provide for direct measurement and assessment of the bondline characteristics and bondline integrity directly at or within the cured bondline 32 itself.

Figure 6:
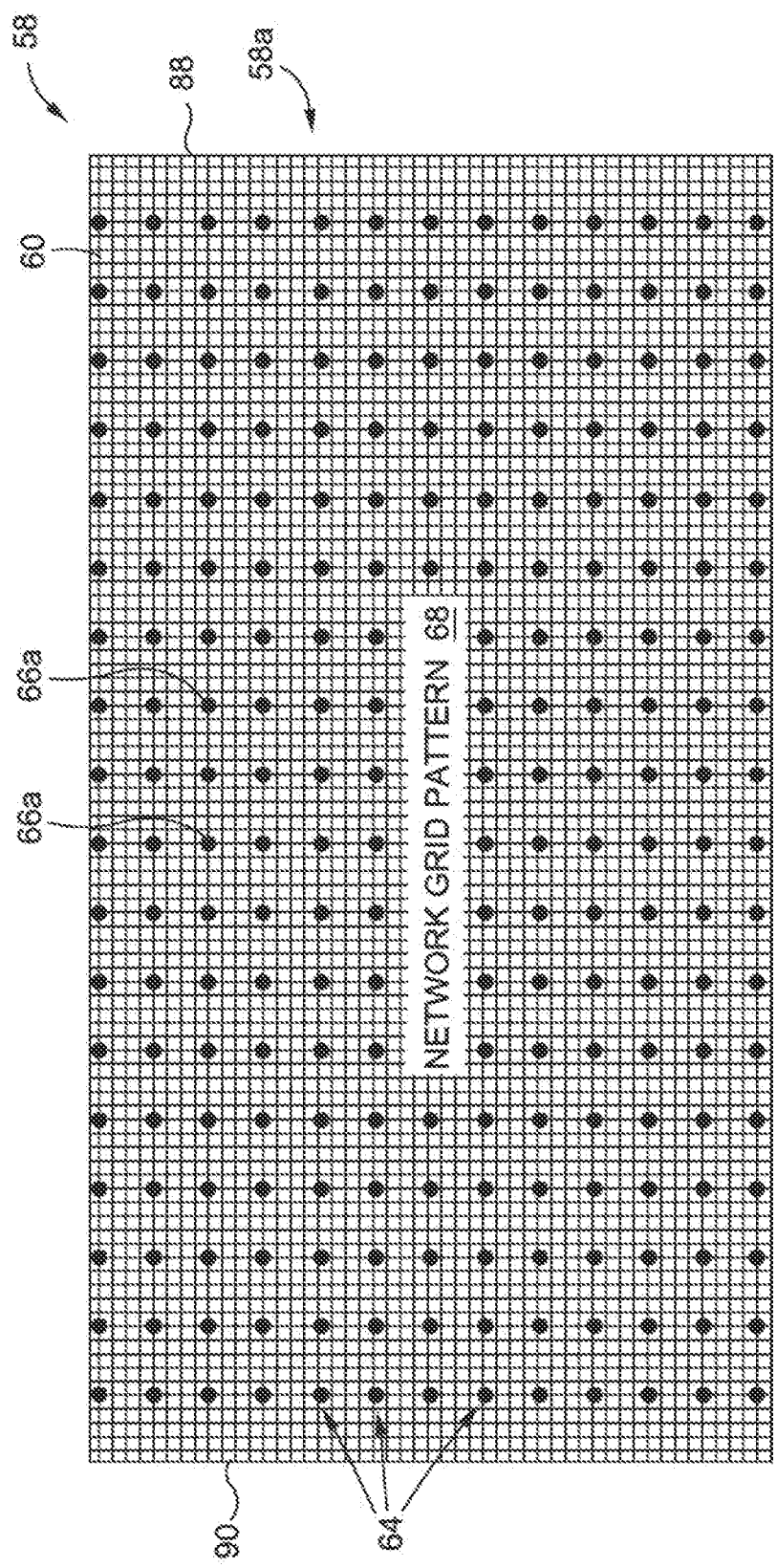
FIG. 6 is an illustration of a top view of one of the embodiments of a scrim ply layer with active sensor nodes.

The sensor elements 66 preferably have modalities based on ultrasonic wave propagation and electromechanical impedance. In order to enable the smart scrim ply layer 58, the sensor elements 66 may be integrated into the woven or random mat fiber layer of the scrim material. In one embodiment, scrim material with the sensor elements 66 may be laminated into the adhesive layer 52 to provide an integrated film adhesive scrim ply layer 58 (see FIG. 6) with sensing capabilities. FIG. 6 is an illustration of a top view of one of the embodiments of the scrim ply layer 58 in the form of a scrim ply layer 58*a* with an electrical sensor network 64 having sensor elements 66 in the form of active sensor nodes 66*a* integrated into or attached onto the scrim ply layer 58. As shown in FIG. 6, the sensor nodes 66*a* form a network grid pattern 68. As shown in FIGS. 4A and 6, the scrim ply layer 58 has a first side 60 (see FIGS. 4A and 6), a second side 62 (see FIG. 4A), a first end 88 (see FIG. 6) and a second end 90 (see FIG. 6).

Figure 5A:
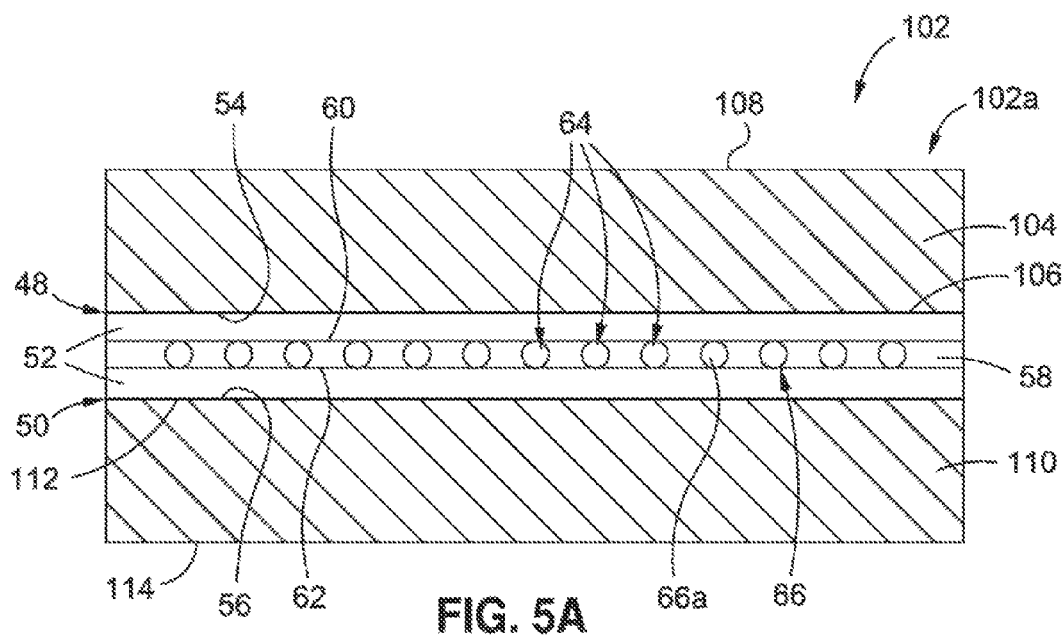
FIG. 5A is an illustration of a partial cross-sectional view of an embodiment of a bonded structure having one of the embodiments of the electrical sensor network of the disclosure.
Figure 5B:
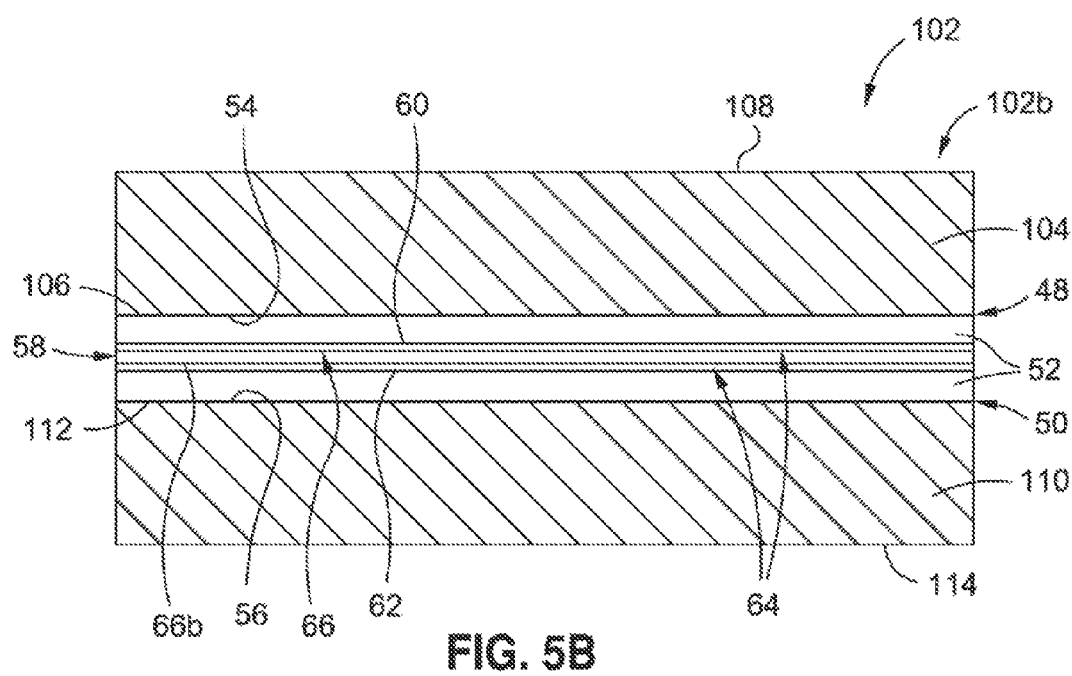
FIG. 5B is an illustration of a partial cross-sectional view of another embodiment of a bonded structure having another one of the embodiments of the electrical sensor network of the disclosure.
Figure 7:
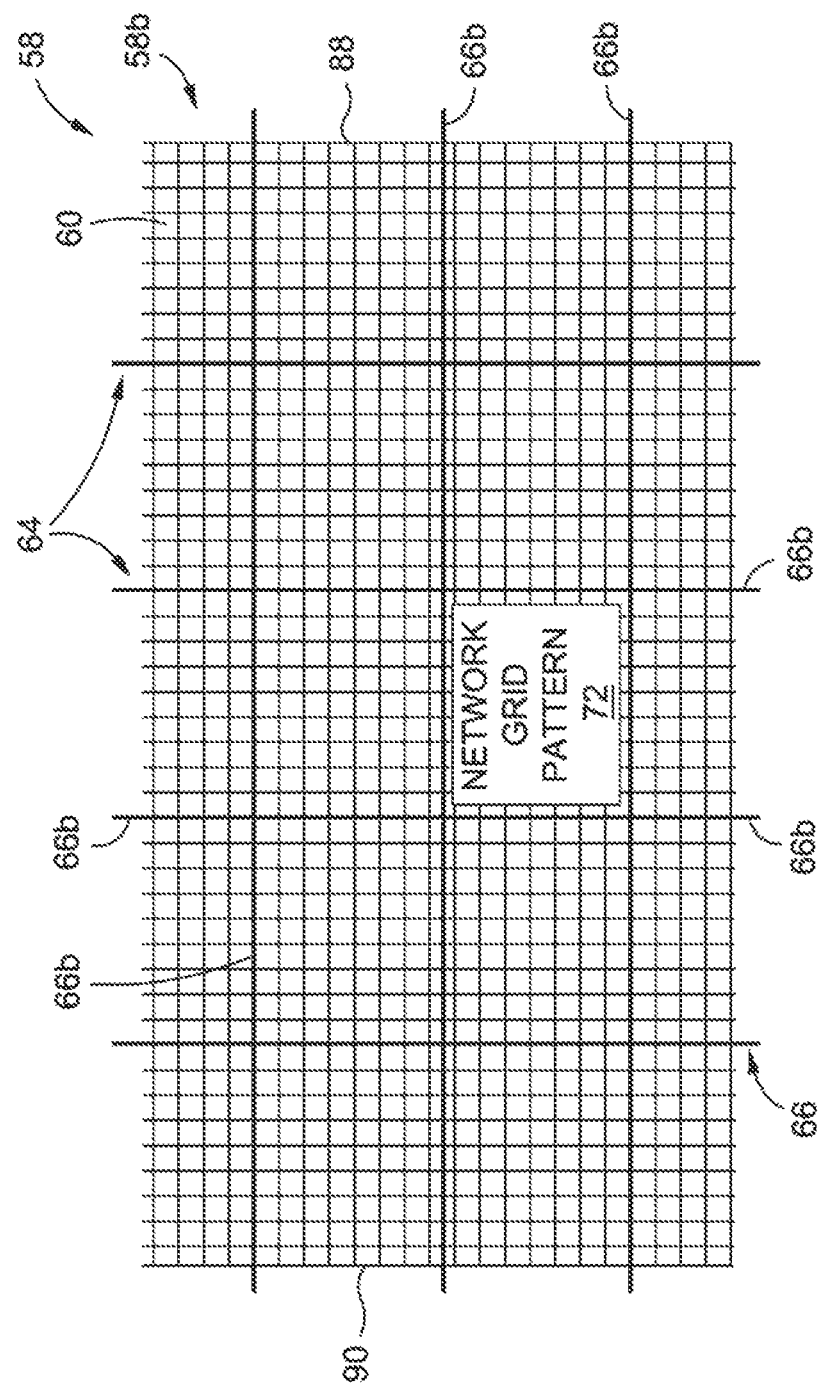
FIG. 7 is an illustration of a top view of another one of the embodiments of a scrim ply layer with sensor fibers.

In another embodiment, sensor elements 66 may be attached or integrated into an existing or known scrim ply layer 58 (see FIG. 7) integrated with the adhesive layer 52. FIG. 7 is an illustration of a top view of another one of the embodiments of the scrim ply layer 58 in the form of a scrim ply layer 58*b* with an electrical sensor network 64 having sensor elements 66 in the form of active sensor fibers 66*b* integrated into or attached onto the scrim ply layer 58. As shown in FIG. 7, the sensor fibers 66*b* form a network grid pattern 72. As shown in FIGS. 5B and 7, the scrim ply layer 58 has a first side 60 (see FIGS. 5B and 7), a second side 62 (see FIG. 5B), a first end 88 (see FIG. 7) and a second end 90 (see FIG. 7).

As shown in FIG. 2, the system 30 further comprises an electrical power source 74 for providing electrical power to the electrical sensor network 64. The electrical power source 74 may comprise batteries, voltage, RFID (radio frequency identification), magnetic induction transmission, or another suitable electrical power source. The electrical power source 74 is preferably wireless.

As shown in FIG. 2, the system 30 further comprises a digital data communications network 76 for retrieving and processing data from the electrical sensor network 64. The digital data communications network 76 is preferably wireless. The digital data communications network 76 may comprise a data retrieval system 78 for retrieving data from the electrical sensor network 64. The data retrieval system 78 may comprise RFID, a radio transceiver (a device that has both a transmitter and a receiver which are combined and share common circuitry or a single housing), or another suitable data retrieval system.

The electrical sensor network 64 monitors adhesive integrity 82 (see FIG. 2) within the cured bondline 32 on demand by interpreting changes in local dynamic responses 84 (see FIG. 2) and electromechanical properties 86 (see FIG. 2) directly measured at or within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded structural assembly 34. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 2, the digital data communications network 76 may further comprise a data processing system 80 for processing data from the electrical sensor network 64. The data processing system 80 may comprise, for example, a known computer processor (not shown), a database (not shown), and a data storage and management system (not shown).

The system 30 monitors adhesive integrity 82 within the cured bondline 32 of the bonded structural assembly 34. Preferably, the system 30 is used for monitoring adhesive integrity at or within the cured bondline 32 of bonded structural assemblies 34, such as bonded structural assemblies for use in aircraft 10 (see FIG. 1), spacecraft, aerospace vehicles, space launch vehicles, rockets, satellites, rotorcraft, watercraft, boats, trains, automobiles, trucks, buses, architectural structures, or other suitable vehicles and structures.

Figure 3:
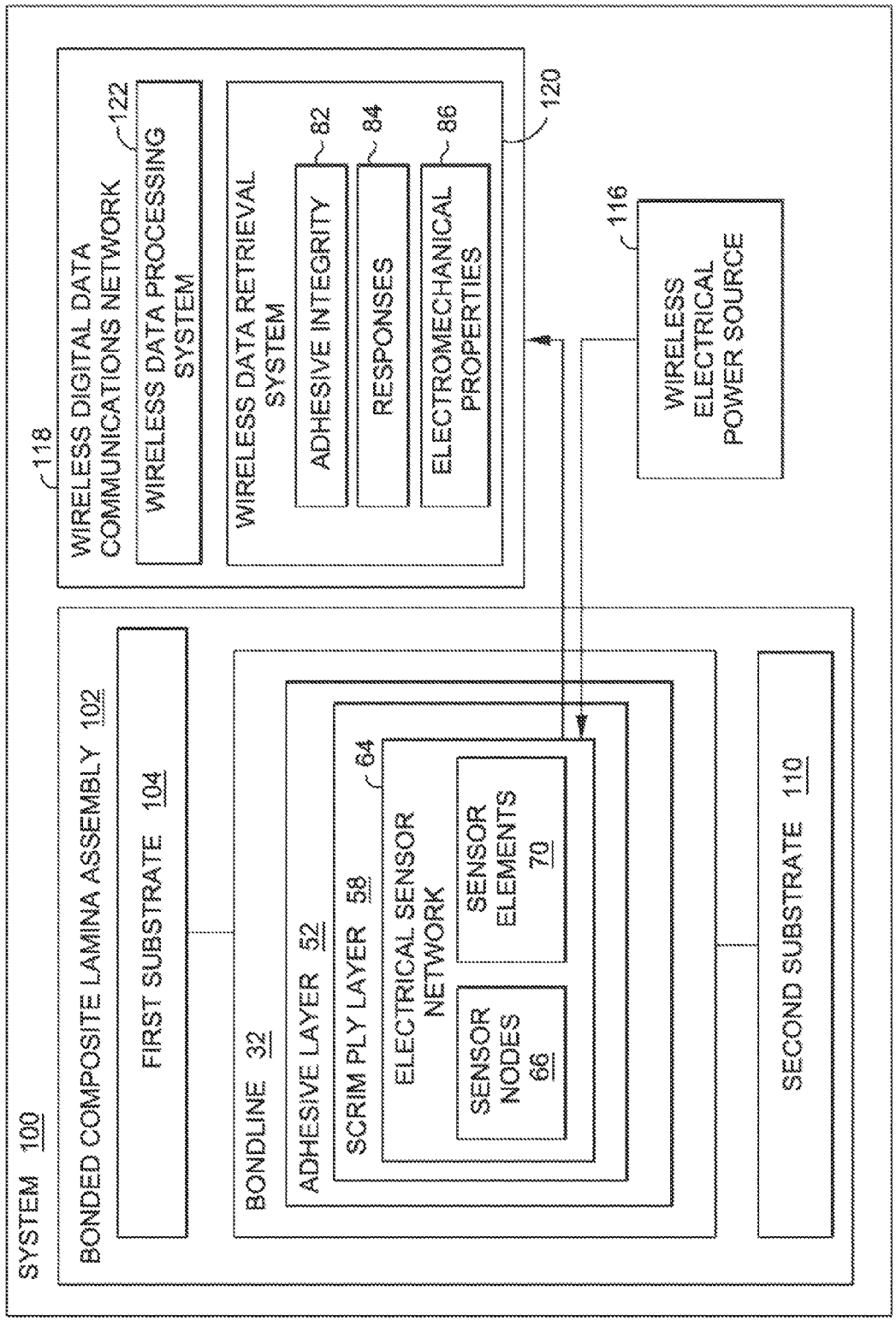
FIG. 3 is an illustration of a block diagram of another one of the embodiments of a system for monitoring adhesive integrity of the disclosure.

FIG. 3 is an illustration of a block diagram of another one of the embodiments of a system 100 for monitoring adhesive integrity within the cured bondline 32 of a bonded composite lamina assembly 102. The system 100 comprises the bonded composite lamina assembly 102 have the cured bondline 32. As shown in FIGS. 5A-5B, the bonded composite lamina assembly 102 may comprise a first substrate 104 and a second substrate 110. The first substrate 104 has a first side 106 and a second side 108. The second substrate 110 has a first side 112 and a second side 114. The first substrate 104 and the second substrate 110 are preferably both made of a composite material comprising polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. FIG. 5A is an illustration of a partial cross-sectional view of an embodiment of a bonded structure 102*a* having one of the embodiments of the electrical sensor network 64 of the disclosure. As shown in FIG. 5A, the electrical sensor network 64 comprises sensor elements 66 comprising active sensor nodes 66*a*. FIG. 5B is an illustration of a partial cross-sectional view of another embodiment of a bonded structure 102*b* having another one of the embodiments of the electrical sensor network 64 of the disclosure. As shown in FIG. 5B, the electrical sensor network 64 comprises sensor elements 66 comprising active sensor fibers 66*b*.

As shown in FIGS. 5A-5B, the cured bondline 32 of the bonded structural assembly 102 comprises adhesive layer or layers 52. The adhesive layer or layers 52 may comprise an adhesive material such as an epoxy adhesive, a polyurethane adhesive, a toughened acrylic adhesive, or another suitable adhesive. The cured bondline 32 further comprises a scrim ply layer 58 integrated with the adhesive layer or layers 52. As shown in FIG. 5A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is multifunctional and acts as an adhesive layer by being integrated in the adhesive layer 52 and also acts as a bondline monitoring system. The cured bondline 32 further comprises an electrical sensor network 64 integrated with the scrim ply layer 58. The electrical sensor network 64 preferably comprises a plurality of spaced sensor elements 66 comprising active sensor nodes 66*a* (see FIG. 5A), active sensor fibers 66*b* (see FIG. 5B), active sensor wires (not shown), sensor fiber optic wires (not shown), sensor coatings on fibers (not shown), carbon nanotubes (not shown), passive sensors, or another suitable sensor element. The sensor elements 66 preferably have modalities based on ultrasonic wave propagation and electromechanical impedance. The monitoring system 100 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 3, the system 100 further comprises a wireless electrical power source 116 for providing electrical power to the electrical sensor network 64. The wireless electrical power source 74 may comprise batteries, voltage, RFID (radio frequency identification), magnetic induction transmission, or another suitable wireless electrical power source.

As shown in FIG. 3, the system 100 further comprises a wireless digital data communications network 118 for retrieving and processing data from the electrical sensor network 64. The wireless digital data communications network 118 may comprise a wireless data retrieval system 120 for retrieving data from the electrical sensor network 64. The wireless data retrieval system 120 may comprise RFID, a radio transceiver, or another suitable data retrieval system. The electrical sensor network 64 monitors adhesive integrity 82 (see FIG. 3) within the cured bondline 32 on demand by interpreting changes in local dynamic responses 84 (see FIG. 3) and electromechanical properties 86 (see FIG. 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded composite lamina assembly 102. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 3, the wireless digital data communications network 118 may further comprise a wireless data processing system 122 for processing data from the electrical sensor network 64. The wireless data processing system 122 may comprise, for example, a known a computer processor (not shown), a database (not shown), and a data storage and management system (not shown).

The system 100 monitors adhesive integrity within the cured bondline 32 of the bonded composite lamina assembly 102. Preferably, the system 100 is used for monitoring adhesive integrity within the cured bondline 32 of bonded composite lamina assemblies 102, such as bonded composite lamina assemblies used in aircraft, spacecraft, aerospace vehicles, space launch vehicles, rockets, satellites, rotorcraft, watercraft, boats, trains, automobiles, trucks, buses, architectural structures, or other suitable vehicles and structures.

Figure 8:
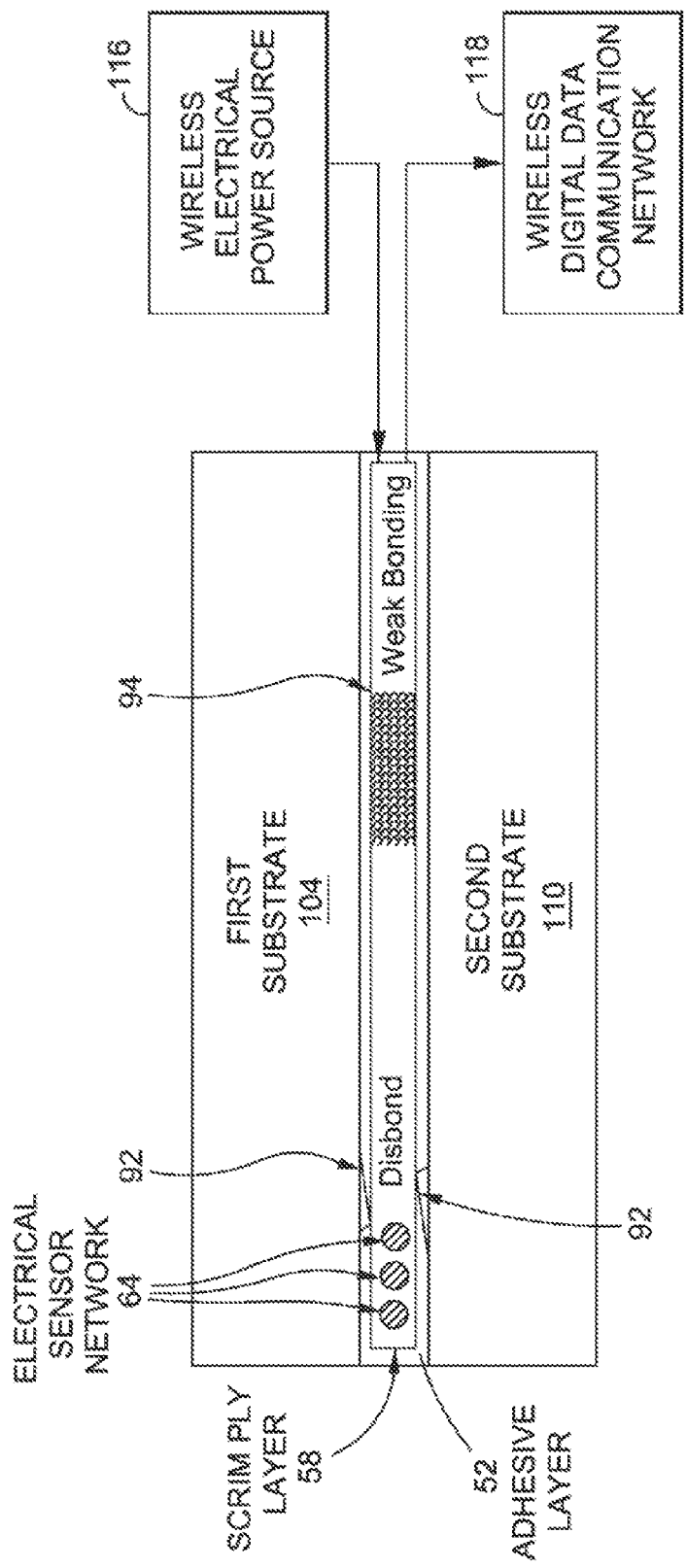
FIG. 8 is an illustration of a schematic diagram of one of the embodiments of a system of the disclosure showing detection of disbonds and weak bonding.

FIG. 8 is an illustration of a schematic diagram of one of the embodiments of the system 100 of the disclosure showing detection of disbonds 92 and weak bonding 94. FIG. 8 shows the first substrate 104 bonded to the second substrate 110 with the scrim ply layer 58 integrated with the adhesive layer 52, and the scrim ply layer 58 having the electrical sensor network 64 integrated with the scrim ply layer 58. The wireless electrical power source 116 provides electrical power to the electrical sensor network 64 of the system 100. The adhesive layer 52 with the scrim ply layer 58 is shown with disbonds 92 and weak bonding 94. The wireless digital data communication network 118 processes the disbond 92 and weak bonding 94 data from the electrical sensor network 64 to monitor the health of the system 100.

Figure 9:
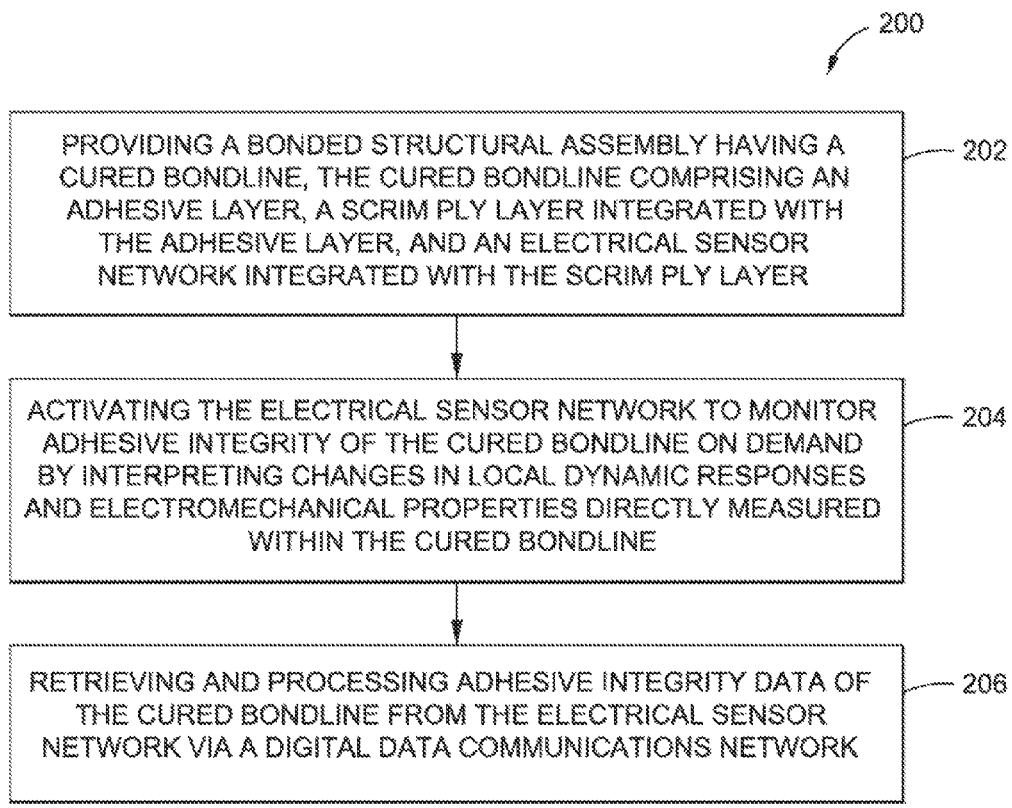
FIG. 9 is an illustration of a flow diagram of an embodiment of a method for monitoring adhesive integrity of the disclosure.

In another embodiment of the disclosure, there is provided a method 200 for monitoring adhesive integrity within a cured bondline 32 (see FIGS. 2, 3) of a bonded structural assembly 34 (see FIG. 2). FIG. 9 is an illustration of a flow diagram of an embodiment of a method 200 for monitoring adhesive integrity within the cured bondline 32. The method 200 comprises step 202 of providing the bonded structural assembly 34 (see FIGS. 4A-4C) having the cured bondline 32. The bonded structural assembly 34 may preferably comprise a bonded composite lamina assembly 102 (see FIG. 3). As discussed above and as shown in FIGS. 4A-4C, the bonded structural assembly 34 may comprise first structure 36 and second structure 42. The first structure 36 may be made of a composite material, a metal material, a combination thereof, or another suitable material. The second structure 36 may be made of a composite material, a metal material, a combination thereof, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Preferably, the metal material for the first structure 36 and/or the second structure 42 comprises aluminum, stainless steel, titanium, alloys thereof, or another suitable metal or metal alloy.

As discussed above, the cured bondline 32 comprises the adhesive layer 52, the scrim ply layer 58 integrated with the adhesive layer 52, and the electrical sensor network 64 integrated with the scrim ply layer 58. As shown in FIG. 4A, the adhesive layer 52 may comprise a first side 54 and a second side 56. As discussed above, the adhesive layer 52 may comprise an adhesive material such as an epoxy adhesive, a polyurethane adhesive, a toughened acrylic adhesive, or another suitable adhesive. As discussed above, the scrim ply layer 58 integrated with the adhesive layer 52 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 may be multifunctional and act as an adhesive layer by being integrated in the adhesive layer 52 and may also act as a bondline monitoring system. As discussed above, the electrical sensor network 64 may comprise a plurality of spaced sensor elements 66 comprising active sensor nodes 66*a*, active sensor fibers 66*b*, active sensor wires (not shown), sensor fiber optic wires (not shown), sensor coatings on fibers (not shown), carbon nanotubes (not shown), passive sensors, or another suitable sensor element. The sensor elements 66 preferably have modalities based on ultrasonic wave propagation and electromechanical impedance. The method 200 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 9, the method 200 further comprises step 204 of activating the electrical sensor network 64 (see FIGS. 4A-4C) to monitor adhesive integrity 82 of the cured bondline 32 on demand by interpreting changes in local dynamic responses 84 and electromechanical properties 86

(see FIG. 2) directly measured within the cured bondline 32. Preferably, the electrical sensor network 64 is activated with an electrical power source 74 (see FIG. 2), and more preferably, with a wireless electrical power source 116 (see FIG. 3). The electrical power source 74 or wireless electrical power source 116 may comprise batteries, voltage, RFID (radio frequency identification), magnetic induction transmission, or another suitable wireless electrical power source.

As shown in FIG. 9, the method 200 further comprises step 206 of retrieving and processing adhesive integrity data of the cured bondline 32 from the electrical sensor network 64 via the digital data communications network 76 (see FIG. 2). Preferably, the digital data communications network is a wireless digital data communications network 118 (see FIG. 3). The digital data communications network 76 may comprise a data retrieval system 78 for retrieving data from the electrical sensor network 64. The data retrieval system 78 may comprise RFID, a radio transceiver, or another suitable data retrieval system. The wireless digital data communications network 118 may comprise a wireless data retrieval system 120 for retrieving data from the electrical sensor network 64. The electrical sensor network 64 monitors adhesive integrity 82 (see FIGS. 2, 3) within the cured bondline 32 on demand by interpreting changes in local dynamic responses 84 (see FIGS. 2, 3) and electromechanical properties 86 (see FIGS. 2, 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline of the bonded structural assembly. The integrity of the cured bondline 32 may be determined by interpreting changes in local dynamic responses 84 and electromechanical properties 86 directly measured at or within the cured bondline 32.

The digital data communications network 76 may further comprise a data processing system 80 for processing data from the electrical sensor network 64. The wireless digital data communications network 118 may further comprise a wireless data processing system 122 for processing data from the electrical sensor network 64. The data processing system 80 and the wireless data processing system 122 may comprise, for example, a known computer processor (not shown), a database (not shown), and a data storage and management system (not shown).

The method 200 monitors adhesive integrity within the cured bondline 32 of the bonded structural assembly 34, and preferably, monitors adhesive integrity within the cured bondline 32 of the bonded composite lamina assembly 102. Preferably, the method 200 is used for monitoring adhesive integrity within the cured bondline 32 of bonded structural assemblies 34, preferably bonded composite lamina assemblies 102, such as used in aircraft, spacecraft, aerospace vehicles, space launch vehicles, satellites, rotorcraft, watercraft, boats, trains, automobiles, trucks, buses, architectural structures, or other suitable vehicles and structures.

Embodiments of the monitoring systems 30, 100 and monitoring method 200 provide for the integration of active sensing materials into an adhesive scrim ply layer 58 to create a multifunctional system or matrix capable of serving as both an adhesive layer and a bondline monitoring system. The sensor elements 66 integrated into the adhesive scrim ply layer 58 matrix interpret changes within the local dynamic responses 84 and the electromechanical properties 86 measured within the bondline interface, and the sensor elements 66 may assess key characteristics such as disbonds, strain levels, moisture ingression, materials changes, cracks, voids, delamination, porosity, and/or other key characteristics at or within the cured bondline interface. Embodiments of the monitoring systems 30, 100 and monitoring method 200 may utilize various sets of active sensor elements 66, such as sensing materials with modalities based on ultrasonic wave propagation and electromechanical impedance based on the scrim meshing pattern, to perform as a power and information network. Activation of the system and data retrieval may be performed wirelessly using a wireless electrical power source 116, a wireless data retrieval system 120, and a wireless data processing system 122 for interpretation of data in situ at the cured bondline 32 of the structural assembly such as the bonded composite lamina assembly 102. Embodiments of the monitoring systems 30, 100 and monitoring method 200 provide a cured bondline 32 with an embedded multifunctional scrim ply layer 58 to monitor on demand or continuously for a change in the bondline interface adhesive integrity quality during both manufacturing and in-service. Such cured bondlines or bonded joints may reduce the overall weight of the structures and structural components by reducing the volume of heavy joints based on the use of fasteners. Bonded joints accomplish this, in part, by spreading the load over a larger footprint.

Embodiments of the monitoring systems 30, 100 and monitoring method 200 may provide monitoring of adhesive integrity at or within the cured bondline 32 in bonded structural assemblies used in aircraft, spacecraft, aerospace vehicles, space launch vehicles, rockets, satellites, rotorcraft, watercraft, boats, trains, automobiles, trucks, buses, and other suitable transport vehicles and structures. Embodiments of the monitoring systems 30, 100 and monitoring method 200 may provide in situ non-destructive systems and method for characterizing bonding properties and ensuring the bondline integrity of structurally bonded parts continuously throughout the service lifetime of the hardware and structurally bonded parts.

Embodiments of the monitoring systems 30, 100 and monitoring method 200 have the ability to interrogate the cured bondline while the structure or structural component parts are in-service; may decrease costs and flow time to the process of assuring bondline integrity; may be carried out on demand on a real time basis or continuously on a real time basis so that the information about the bondline integrity is available at all times; and, may predict and monitor the integrity, health and fitness of cured bondlines or bonded joints located remotely, interior, or beneath the structural surface without having to disassemble or remove structures or structural components or drill holes into the structures or structural components for insertion of any measurement tools. Moreover, embodiments of the monitoring systems 30, 100 and monitoring method 200 may provide for an internal electrical sensor network and internal sensors at or within the cured bondline to provide for direct measurement and assessment of the bondline characteristics and bondline integrity directly at or within the bondline itself. Finally, embodiments of the monitoring systems 30, 100 and monitoring method 200 may be used to predict deterioration or weaknesses directly at or within the cured bondline or bonded joint prior to the actual development of such deterioration or weaknesses, and thus, may increase reliability of the structure or structural component parts, may increase the safety of the adhesive bondline, and may reduce overall manufacturing and maintenance costs over the life of the structure or structural component parts.

Figure 10:
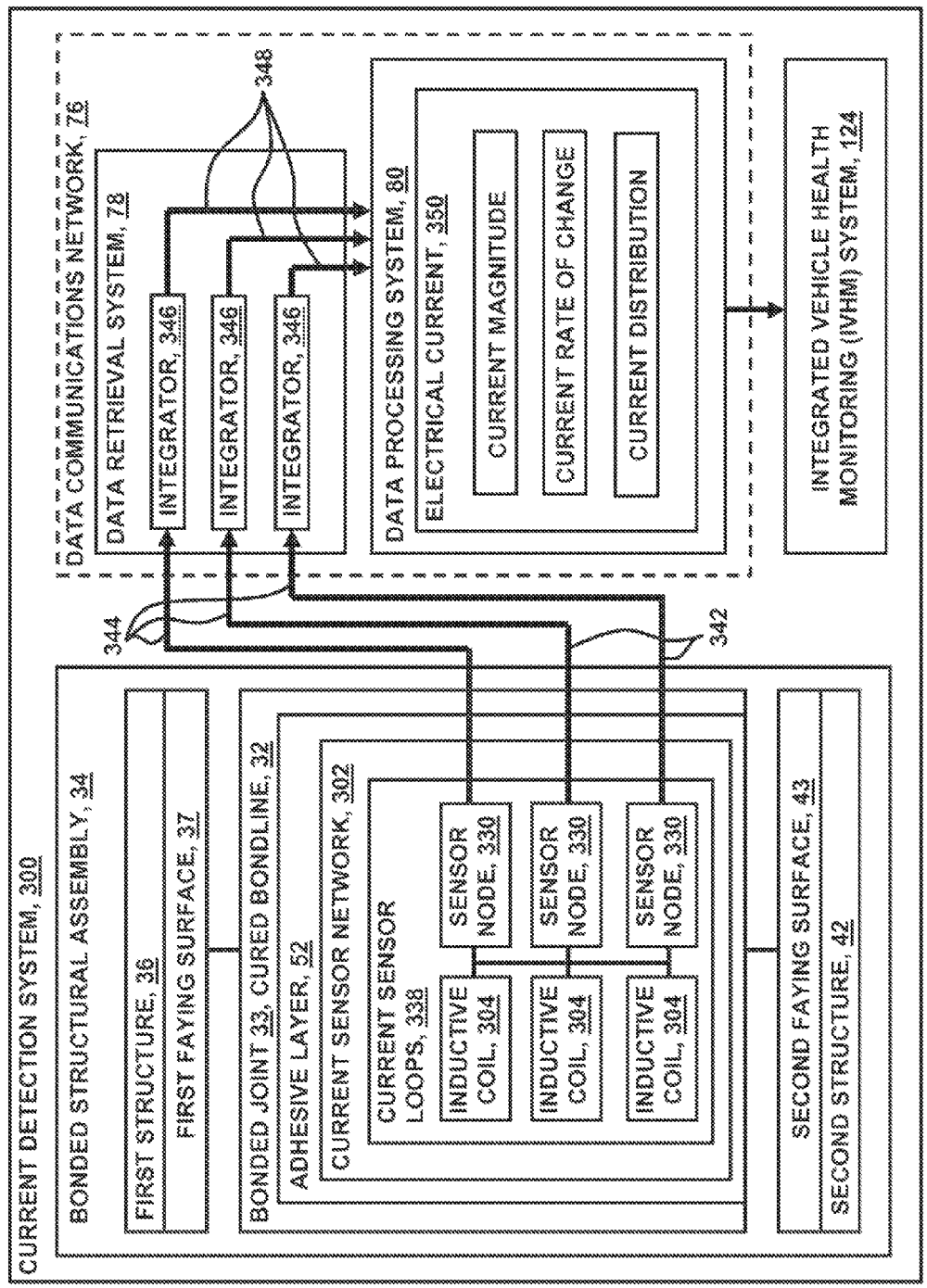
FIG. 10 is an illustration of a block diagram of an embodiment of a system for detecting and monitoring electrical current flow through a bonded joint.

FIG. 10 shows a block diagram of an embodiment of a current detection system 300 for detecting and monitoring electrical current 350 (FIG. 11) flow through a bonded joint 33 of a bonded structural assembly 34. As indicated above, the bonded structural assembly 34 may include a first structure 36 and a second structure 42. The first structure 36 and/or the second structure 42 may be formed of composite material such as fiber-reinforced polymer matrix material. However, the first structure 36 and/or the second structure 42 may be formed of metallic material, ceramic material, or a combination of composite material, ceramic material, and metallic material. The first structure 36 has a first faying surface 37 and the second structure 42 has a second faying surface 43. The first and second faying surfaces 37, 43 may be bonded together by an adhesive layer 52 of a cured bondline 32 located between the first faying surface 37 and the second faying surface 43. As mentioned above, the adhesive layer 52 may be formed of a material selected from the group comprising epoxy adhesives, polyurethane adhesives, and acrylic adhesives, or any other type of structural adhesive. In some examples, the structural assembly 34 may be configured with no mechanical fasteners in the bonded joint 33. However, in other examples, one or more mechanical fasteners (not shown) or other mechanical features may be included in the bonded joint 33 to mechanically assist in coupling the first structure 36 to the second structure 42.

Figure 11:
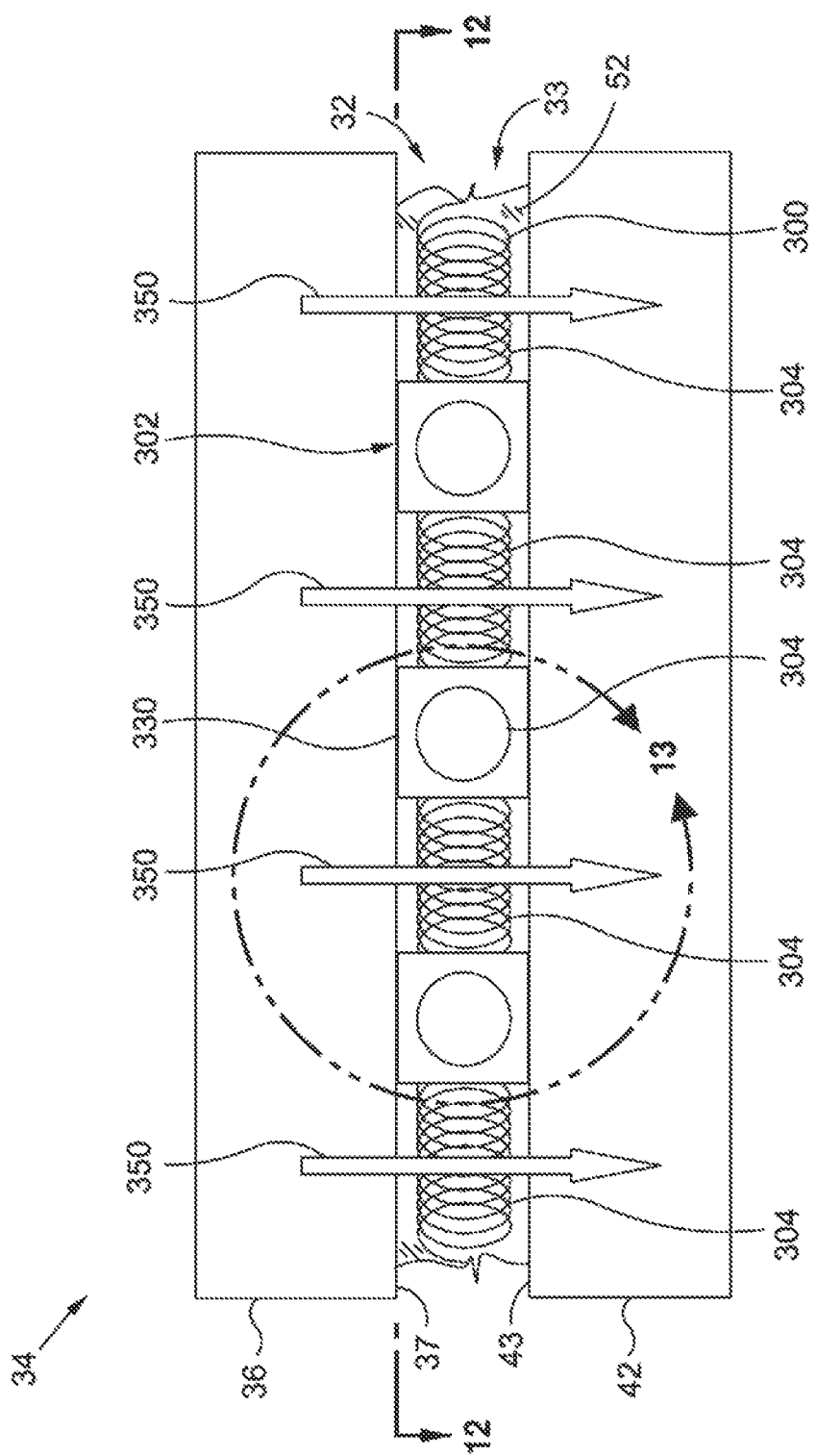
FIG. 11 is an illustration of a partial cross-sectional view of a structural assembly showing an embodiment of a current sensor network embedded in an adhesive layer of a bonded joint joining the first and second structure of the structural assembly.

In FIG. 10, the current detection system 300 may further include a current sensor network 302 that may be embedded in the adhesive layer 52 of the cured bondline 32 of the structural assembly 34. In an example, the current sensor network 302 may include a plurality of inductive coils 304 and a plurality of current sensor nodes 330 electrically interconnecting the inductive coils 304. In the example shown, the inductive coils 304 and the current sensor nodes 330 may be arranged to form a plurality of current sensor loops 338 (FIG. 11). As described in greater detail below, an electrical current 350 flowing or passing through the adhesive layer 52 may have a magnetic field 352 (FIG. 11) associated with the electrical current 350. The electrical current 350 passing through the adhesive layer 52 may be described as a transient current or a current pulse passing through the adhesive layer 52 along a direction from the first structure 36 to the second structure 42, or vice versa. The electrical current 350 flowing through the adhesive layer 52 may be the result of a lighting strike or other electrical charge applied to the structural assembly 34 or flowing into the structural assembly 34 from another location on a vehicle or structure containing the structural assembly 34.

Induced current 306 (FIG. 13) may be generated in the inductive coils 304 of the current sensor loops 338 when electrical current 350 is flowing through the adhesive layer 52. The induced current 306 may be generated as a result of the magnetic field 352 associated with the electrical current 350 through the adhesive layer 52. The magnetic field 352 may induce a relatively low-magnitude induced current 306 in the inductive coils 304. For example, the induced current 306 may be on the order of microamps or milliamps, and may be generated in response to an electrical current 350 passing through the adhesive layer 52 on the order of from 100 milliamps up to 100 amps or more. For example, electrical current 350 passing through a structural assembly 34 as a result of a lightning strike may be on the order of up to 100,000 amps or more, and may be associated with a voltage of up to 100 kilovolts or more.

In FIG. 10, the current detection system 300 may further include a digital data communications network 76 which may be located external to the cured bondline 32. The digital data communications network 76 may be coupled to the current sensor nodes 330 by one or more signal wires 342. The digital data communications network 76 may receive and process current signals 344 which may be generated by electronic circuitry (not shown) included in the current sensor nodes 330. The current signals 344 may be representative of the induced current 306. For example, the current signal 344 generated by a given current sensor node 330 may be proportional to the magnitude of the induced current 306 in one or more of the inductive coils 304 that are electrically connected to the given current sensor node 330. In some examples, the current signal 344 generated by a given current sensor node 330 may be proportional to the local magnitude (e.g., amperage) of the electrical current 350 passing through the adhesive layer 52 at a location adjacent to the given current sensor node 330. In this regard, the magnitude of the induced current 306 in the inductive coils 304 embedded throughout the adhesive layer 52 may be different at different locations of the adhesive layer 52, as described in greater detail below.

The digital data communications network 76 may use the current signals 344 to detect and monitor electrical current 350 passing through one or more portions of the cured bondline 32. In some examples, the digital data communications network 76 may include a data retrieval system 78 for receiving current signals 344 from the current sensor nodes 330. The data retrieval system 78 may include one or more current integrators 346. The current integrators 346 may be electrically connected to the current sensor nodes 330. In some examples, each one of the current sensor nodes 330 may be electrically connected to a dedicated current integrator 346. A current integrator 346 may integrate the induced current 306 over time and may generate an output signal 348 which may be proportional to the magnitude of the current signal 344 received by the current integrator 346.

The digital data communications network 76 may further include a data processing system 80 which may receive the output signals 348 from the data retrieval system 78. As indicated above, the data retrieval system 78 and data processing system 80 may comprise, for example, a known computer processor (not shown), a database (not shown), and/or a data storage and management system (not shown). The data processing system 80 may process the output signals 348 to detect, monitor, and/or characterize one or more parameters associated with the electrical current 350 passing through the adhesive layer 52. For example, the digital data communications network 76 may detect the existence of electrical current 350 passing through the cured bondline 32 by comparing the magnitude of the electrical current 350 to a predetermined threshold current value. In other examples, the digital data communications network 76 may characterize the electrical current 350 passing through the adhesive layer 52 by summing the current signals 344 from one or more of the current integrators 346 to determine the total electrical charge of the electrical current 350 passing through the cured bondline 32. The digital data communications network 76 may also characterize the electrical current 350 passing through the adhesive layer 52 by determining the event time (e.g., total elapsed time) during which the electrical current 350 passes through the adhesive layer 52, and/or determining the rate of change of the electrical current 350 as it passes through the adhesive layer 52. In some examples, the digital data communications network 76 may convert the current signals 344 to voltage signals (not shown), and may interpret or analyze the voltage signals to detect, monitor, and/or characterize the electrical current 350 passing through the cured bondline 32.

In FIG. 10, the current detection system 300 may be in communication with an integrated vehicle health management (IVHM) system 124 as may be included in a vehicle such as an aircraft. The digital data communications network 76 may be configured to communicate or transmit the electrical current 350 data to an IVHM system 124 which may, in turn, communicate the electrical current 350 data to an external maintenance tracking system (not shown) and/or to appropriate maintenance personnel to monitor and/or assess the potential need for inspection of one or more bonded joints 33 that may have been subjected to relatively high-intensity electrical current 350 flow as detected by the current detection system 300. For example, a vehicle such as an aircraft 10 (FIG. 1) may include a plurality of bonded structural assemblies 34 each including one or more bonded joints 33. The bonded joints 33 may include one or more cured bondlines 32 incorporating a current sensor network 302 embedded in an adhesive layer 52 of the cured bondline 32. The current sensor network 302 in the cured bondline 32 of the different bonded structural assemblies 34 may be in communication with an IVHM system 124. The IVHM system 124 may monitor the electrical current 350 passing through each cured bondline 32 of the bonded structural assemblies 34. In the event that one or more of the bonded structural assemblies 34 are subjected to a transient electrical charge such as due to a lightning strike on an aircraft, the IVHM system 124 may determine the magnitude of the lightning-induced electrical charge passing through one or more of the bonded joints 33 at different location in the aircraft 10. In some examples, the IVHM system 124 may record a time-history of the electrical charges passing through different bonded joints 33 of the aircraft 10 to establish a propagation or flow direction or path of the lightning-induced electrical charge as it passes throughout the aircraft 10.

FIG. 11 shows a cross-sectional view of a structural assembly 34 of a first structure 36 adhesively bonded to a second structure 42 at a bonded joint 33. The bonded joint 33 includes a cured bondline 32 contain adhesive bonding the first faying surface 37 of the first structure 36 to the second faying surface 43 of the second structure 42. The cured bondline 32 includes a current sensor network 302 embedded in the adhesive layer 52 of the bonded joint 33. The current sensor network 302 includes a plurality of inductive coils 304 embedded in the adhesive layer 52 and electrically interconnected to one another by a plurality of current sensor nodes 330. Each one of the inductive coils 304 has a lengthwise direction oriented generally parallel to the first and second faying surfaces 37, 43 of the first and second structure 36, 42. An electrical current 350 is shown passing through the adhesive layer 52 along a direction from the first structure 36 to the second structure 42. However, as indicated above, the electrical current 350 may pass through the adhesive layer 52 along a direction from the second structure 42 to the first structure 36. A magnetic field 352 may be associated with the electrical current 350 passing through the adhesive layer 52. As indicated above, the magnetic field 352 may induce an induced current 306 in the inductive coils 304 which may be picked up at the current sensor nodes 330. The current sensor nodes 330 may generate current signals 344 representative of the induced current 306. The current signals 344 may be transmitted via signal wires 342 to the digital data communications network 76 as shown in FIG. 1 and described above.

Figure 12:
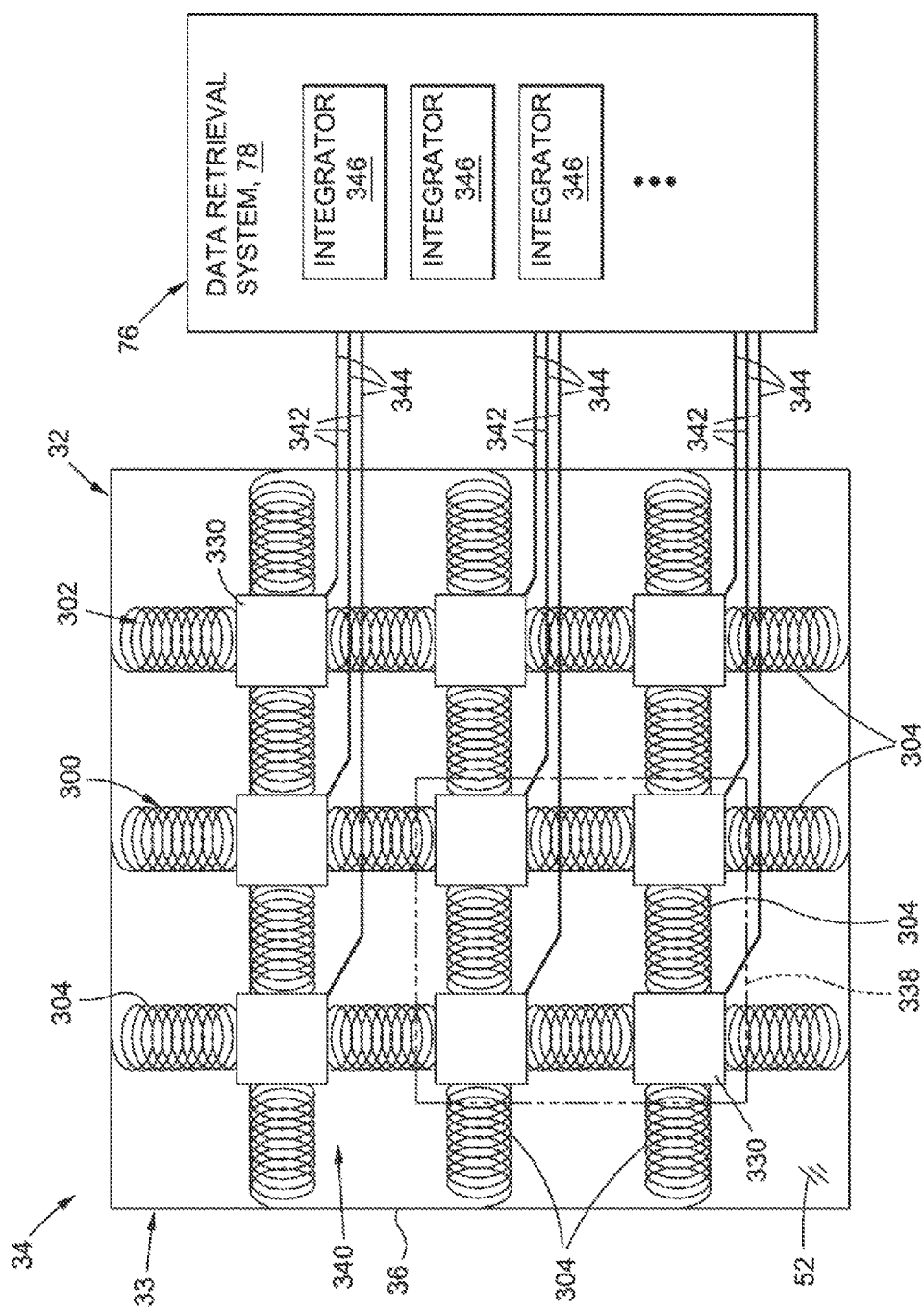
FIG. 12 is an illustration of the top view of an embodiment of a current sensor network as may be embedded in an adhesive layer of the bonded joint.

FIG. 12 shows a top view of an embodiment of a current sensor network 302 as may be embedded in an adhesive layer 52 of a bonded joint 33. In the example shown, the current sensor network 302 is comprised of a plurality of relatively straight sections of inductive coils 304 embedded in the adhesive layer 52. One or more of the inductive coils 304 may be generally straight. One or both of the opposing ends of the inductive coil 304 may be electrically connected to a current sensor node 330. As indicated above, the current sensor network 302 may include a plurality of current sensor nodes 330. Each one of the current sensor nodes 330 may electrically connect two or more inductive coils 304. In this regard, the current sensor nodes 330 may electrically interconnect the inductive coils 304 to form a plurality of current sensor loops 338.

In FIG. 12, the inductive coils 304 and current sensor nodes 330 may be configured such that current sensor loops 338 are arranged in a generally uniformly-spaced grid pattern 340 within the adhesive layer 52 of the cured bondline 32. However, the inductive coils 304 and the current sensor nodes 330 may be arranged in a non-uniform grid pattern 340 (not shown), or in a combination of a non-uniform grid pattern in some portions of the current sensor network 302, and in a uniform grid pattern 340 in other portions of the current sensor network 302. A generally uniform grid pattern 340 of the inductive coils 304 and current sensor nodes 330 along at least a portion of the cured bondline 32 may allow for sensing electrical current 350 at uniformly-spaced locations defined by the grid pattern 340. In this manner, the magnitude of current signals 344 generated at each one of the current sensor nodes 330 relative to one another may be used to determine the mapping or distribution (e.g., the relative magnitude or amperage) of the electrical current 350 at different locations along the length and width of the cured bondline 32. The spacings between current sensor nodes 330 may be selected based upon the desired fidelity with which the distribution of electrical current 350 may be mapped within the cured bondline 32. For example, the current sensor nodes 330 may be spaced apart at spacings of up to 1 inch or more.

Referring still to FIG. 12, at least some of the inductive coils 304 of the current sensor network 302 may be oriented generally orthogonally relative to one another when the current sensor network 302 is viewed along a direction normal to the first and second faying surfaces 37, 43. In such an arrangement, at least one of the current sensor loops 338 may have a generally square shape defined by an inductive coil 304 on each of four sides of the square-shaped current sensor loop 338 and a current sensor node 330 at each corner of the square-shaped current sensor loop 338 as shown in FIG. 12. However, the inductive coils 304 may be arranged in various orientations to provide any one of a variety of different geometrical shapes of the current sensor loops 338. For example, one or more of the inductive coils 304 of a current sensor network 302 may be provided in non-orthogonal arrangements such as to form a grid pattern 340 of triangularly-shaped current sensor loops (not shown) having an inductive coil 304 on three sides and a current sensor node 330 at each vertex of the triangularly-shaped current sensor loops. In addition, the inductive coils 304 are not limited to being provided in a straight shape extending between a pair of current sensor nodes 330. In this regard, one or more of the inductive coils 304 may be provided in a curved shape, or a combination of a curved shape and a straight shape, when the current sensor network 302 is viewed along a direction normal to the first and second faying surface 37, 43s.

Advantageously, the arrangement of the current sensor loops 338 results in the inducement of generally low-amperage induced current 306 in the inductive coils 304 in response to the magnetic field 352 associated with electrical current 350 passing through the adhesive layer 52 from the first structure 36 to the second structure 42, or vice versa. The current sensor loops 338 may advantageously be immune to electromagnetic interference and/or current from another source flowing through external structure (not shown) located adjacent to the first structure 36 and second structure 42. For example, the current sensor network 302 may be immune to current flow through adjacent skin panels or other structure that may be attached to the first structure 36 and/or the second structure 42.

In FIG. 12, the current sensor network 302 may be connected to a data retrieval system 78 of a digital data communications network 76 (FIG. 1). The data retrieval system 78 may be located external to the cured bondline 32 and may receive current signals 344 via signal wires 342 extending through the adhesive layer 52 from the current sensor nodes 330 to one or more external current integrators 346 of the data retrieval system 78. As indicated above, the current integrators 346 may integrate the current signals 344 over time and generate an output signal 348 which may be proportional to the magnitude of the current signal 344 received by the current integrator 346. The output signals 348 may be transmitted to an external data processing system 80 (FIG. 1) for processing the output signals 348 and determining one or more parameters associated with the electrical current 350 passing through the cured bondline 32. In some examples, the current integrators 346 may integrate the induced currents 306 over time and convert the electrical current 350 signal from an analog signal to a digital signal for processing into an electrical current profile (e.g., rate of change of current (I) flow over time (t), dI/dt) associated with the electrical charge passing through the adhesive layer 52 at a location adjacent to a given current sensor node 330.

Figure 13:
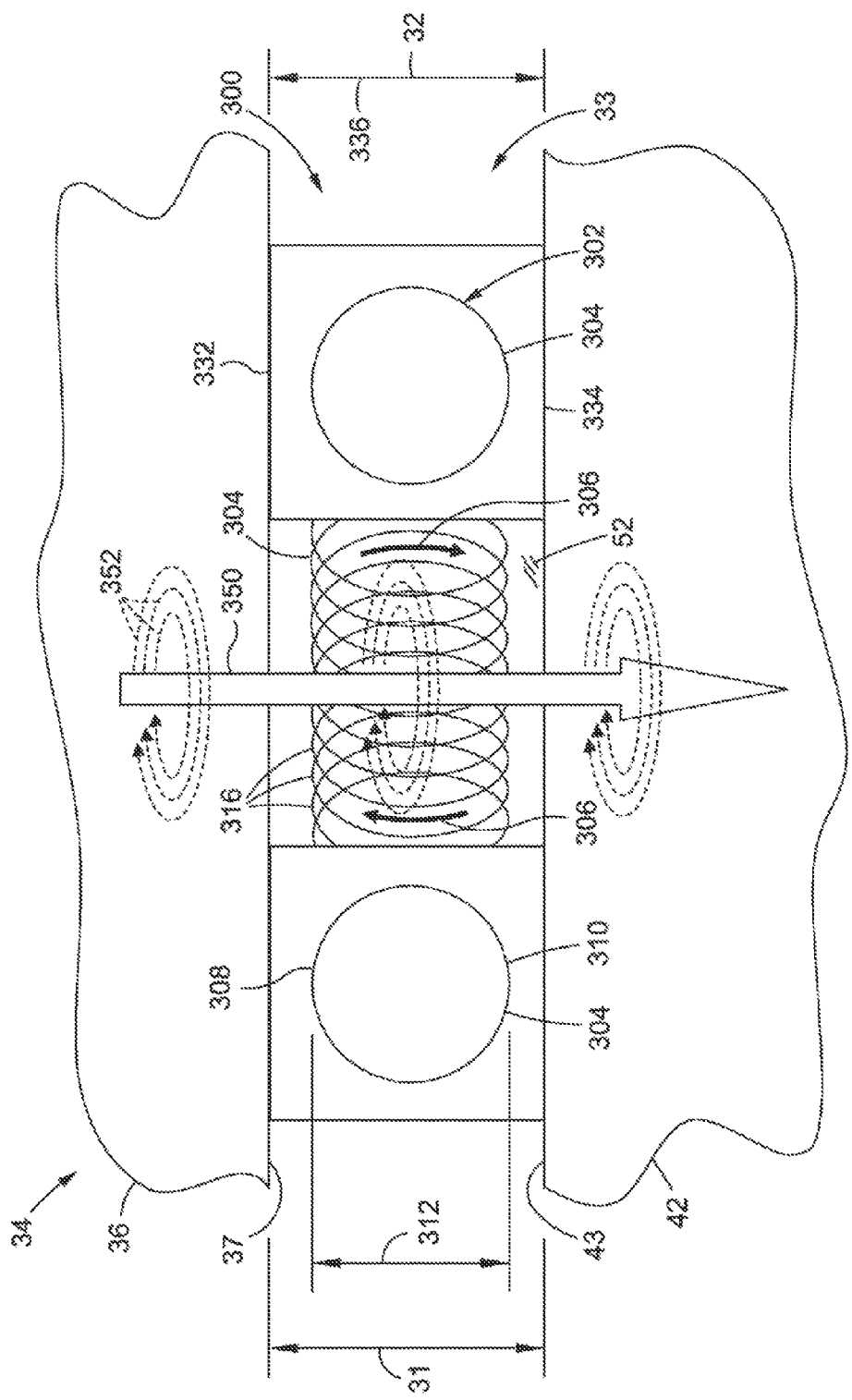
FIG. 13 is an illustration of a partial cross-sectional view of an inductive coil extending between a pair of current sensor nodes of the current sensor network and further illustrating an electrical current passing through the adhesive layer and a magnetic field associated with the electrical current and inducing an induced current in the inductive coil.

FIG. 13 shows a partial cross-sectional view of an inductive coil 304 extending between a pair of current sensor nodes 330 of a current sensor network 302 and further illustrating an electrical current 350 passing through the adhesive layer 52 from the first structure 36 to the second structure 42. Also shown is a magnetic field 352 associated with the electrical current 350. As indicated above, the magnetic field 352 may induce an induced current 306 in the inductive coil 304, and which may be picked up at the current sensor nodes 330 and transmitted in the form of current signals 344 to an external digital data communications network 76 (FIG. 1) configured to process the current signals 344 and detect, analyze, and/or characterize the electrical current 350 passing through the adhesive layer 52 of the cured bondline 32. Alternatively, in an embodiment not shown, one or more of the current sensor nodes 330 may include a current integrator 346 which may generate an output signal 348 based on the induced current 306 in the inductive coils 304. The output signal 348 may then be transmitted via one or more signal wires 342 (FIG. 12) to an external data processing system 80 (FIG. 1).

In FIG. 13, the current sensor network 302 may be provided in a relatively small height enabling the current sensor network 302 to be embedded in relatively thin bondlines of structurally bonded joints 33. In one example, the current sensor network 302 may be sized and configured to fit within a bondline thickness 31 of a cured bondline 32 of no greater than approximately 0.020 inch. The adhesive layer 52 may have an adhesive layer 52 thickness that may be substantially equivalent to the bondline thickness 31. In some examples, the current sensor network 302 may be sized and configured to fit within a bondline thickness 31 of no greater than 0.010 inch or less. In this regard, the inductive coils 304 may be provided in an inductive coil height 312 of no greater than approximately 0.020 inch, and more preferably, in an inductive coil height 312 of no greater than approximately 0.010 inch. Likewise, the current sensor nodes 330 may be provided in a node height 336 of no greater than approximately 0.020 inch and, more preferably, 0.010 inch or less. However, in some examples, the adhesive layer 52 may have a bondline thickness 31 of greater than to a 0.020 inch, which may allow for an increased thickness of the current sensor network 302. In this regard, the inductive coil height 312 and/or the node height 336 may be up 0.030 inch or more.

The inductive coil height 312 of an inductive coil 304 may be defined as the distance between a coil upper side 308 and a coil lower side 310. In some examples, the current sensor network 302 may be configured such that the coil upper side 308 and/or the coil lower side 310 are positioned in non-contacting relation with the first faying surface 37 and/or the second faying surface 43 when the inductive coil 304 is embedded within the adhesive layer 52. The coil upper side 308 and/or the coil lower side 310 may be separated from the first faying surface 37 and/or the second faying surface 43 by a thin layer of adhesive. However, in other examples, the coil upper side 308 and/or the coil lower side 310 may contact the first faying surface 37 and/or the second faying surface 43. In some examples, one or more of the current sensor nodes 330 may be provided in a node height 336 that is substantially equivalent to the desired bondline thickness 31 such that a node upper side 332 and/or a node lower side 334 of at least one current sensor node 330 is in abutting contact with the first faying surface 37 and the second faying surface 43. However, in other examples, one or more of the current sensor nodes 330 may be provided in a node height 336 that is less than the bondline thickness 31 such that a node upper side 332 and/or a node lower side 334 of one or more of the current sensor nodes 330 may be in non-contacting relation to the first faying surface 37 and/or the second faying surface 43. For example, the node upper side 332 and/or the node lower side 334 may be separated from the first faying surface 37 and/or the second faying surface 43 by a thin layer of adhesive.

Each inductive coil 304 may be configured as a generally helically-shaped wire formed as a series of connected 360-degree turns 316. The turns 316 in an inductive coil 304 may be in non-contacting relation to one another and/or may be physically separated and electrically insulated from one another by the adhesive layer 52 within which the inductive coil 304 is embedded. The wire of the inductive coils 304 may have a relative small size (e.g., less than 0.0003 inch diameter) and may be formed of a conductive material such as a metallic material. For example, the inductive coils 304 may be formed of a copper alloy such as copper-nickel, copper-silver, or the inductive coils 304 may be formed of stainless steel, carbon steel, titanium, and other metal alloys or combinations thereof. In some examples, the wires of the inductive coils 304 may be coated with Kapton™ to withstand the high current environment to which a bonded joint 33 may be subjected. The inductive coils 304 of a current sensor network 302 may be substantially similar in geometry, size, and material. However, different portions of a current sensor network 302 may include inductive coils 304 having a different geometry, size, and/or material.

FIG. 14 shows a partial cross-sectional view of an embodiment of a current sensor network 302 wherein the inductive coils 304 have a flattened cross-sectional shape 318 configured as a generally rectangular cross-sectional shape 320 when the inductive coils 304 are viewed from an end of the inductive coil 304 along a lengthwise direction of the inductive coil 304. In this regard, the flattened cross-sectional shape 318 of the inductive coil 304 may result in an inductive coil height 312 that is less than an inductive coil width 314, and is in contrast to the circular cross-sectional shape of the inductive coils 304 having a substantially equivalent inductive coil height 312 and width as shown in FIGS. 11 and 13. Advantageously, a flattened cross-sectional shape 318 of the inductive coil 304 may allow for increased cross-sectional area of the inductive coil 304 while reducing the overall height of the inductive coil 304 to fit within a relative small bondline thickness 31. Increasing the cross-sectional area of the inductive coil 304 by providing the inductive coil 304 in a flattened cross-sectional shape 318 may enhance the ability of the inductive coil 304 to pick up a magnetic field 352, and thereby generate an induced current 306 in response to the magnetic field 352 associated with the electrical current 350 passing through the adhesive layer 52.

FIG. 15 shows a partial cross-sectional view of another embodiment of the current sensor network 302 wherein the inductive coils 304 have an oval cross-sectional shape 322 when viewed from an end of the inductive coil 304 along a lengthwise direction of the inductive coil 304. As may be appreciated, the inductive coils 304 may be provided in any one of a variety of different cross-sectional sizes, shapes and configurations, and are not limited to the rectangular and oval cross-sectional shapes 320, 322 shown in FIGS. 14 and 15. For example, one or more of the inductive coils 304 may have a square cross-sectional shape, a triangular cross-sectional shape, and/or other cross-sectional shapes or combinations thereof.

A current detection system 300 may be incorporated into a structural assembly 34 using a manufacturing method which may include providing a first structure 36 and a second structure 42 to be adhesively bonded together. The method may include preparing the first faying surface 37 of the first structure 36 for bonding such as by abrading the first faying surface 37 to improve the adhesive capability, and may include cleaning and/or treating the first faying surface 37 to facilitate the adhesive bonding process. The second faying surface 43 of the second structure 42 may be prepared for bonding in a similar manner to the first faying surface 37 of the first structure 36. The method may additionally include installing a current sensor network 302 as described above on the first faying surface 37 of the first structure 36. The method may additionally include connecting the current sensor nodes 330 to the digital data communications network 76 using signal wire 342 as shown in FIG. 12. The signal wires 342 may electrically connect one or more of the current sensor nodes 330 to one or more of the current integrators 346. The method may additionally include covering a substantial majority of the first faying surface 37 area with an adhesive layer 52. In this regard, the method may include applying an adhesive layer 52 to the first faying surface 37 in a manner to embed the inductive coils 304 and the current sensor nodes 330 in the adhesive layer 52. The method may further include positioning the second structure 42 over the first structure 36 such that the second faying surface 43 is in contact with the adhesive layer 52. The method may also include allowing the adhesive layer 52 to cure such that the first structure 36 is adhesively bonded to the second structure 42 with the current sensor network 302 embedded within the adhesive layer 52.

Figure 16:
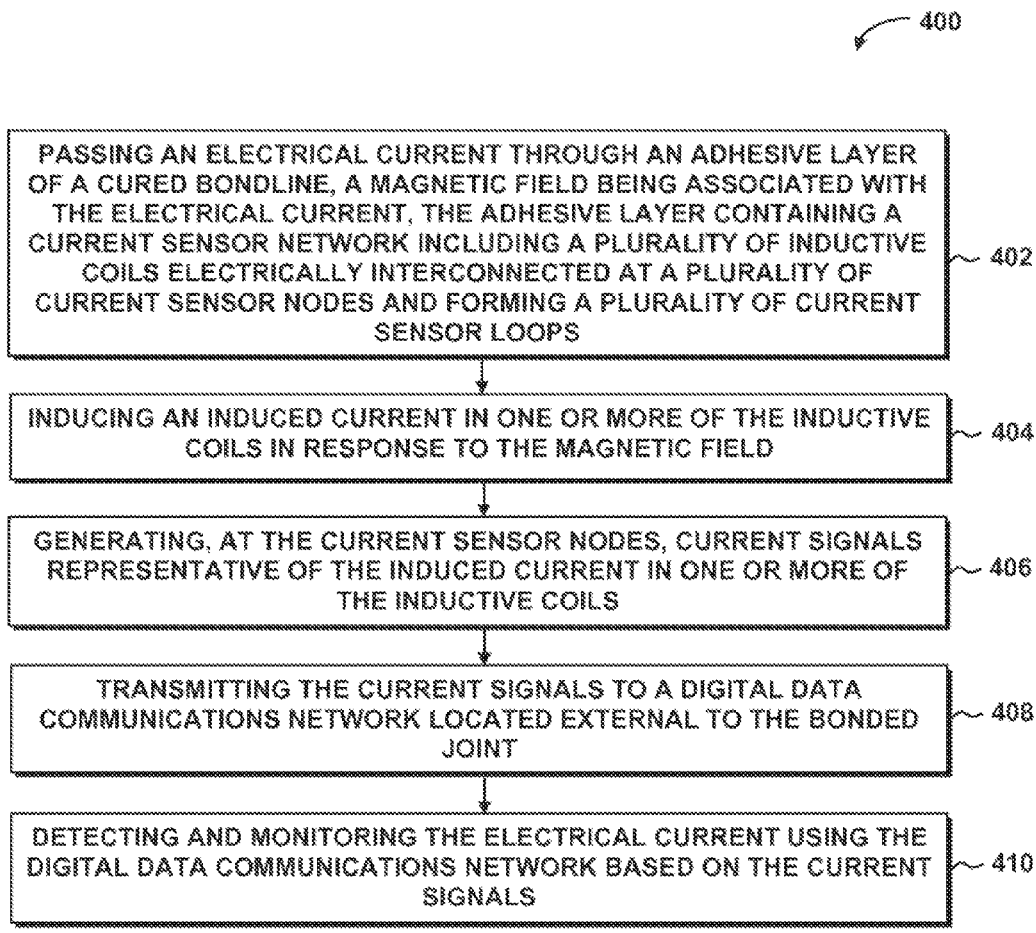
FIG. 16 is an illustration of a flow diagram of an embodiment of a method for monitoring electrical current flow through a cured on line of the bonded structural assembly.

FIG. 16 is an illustration of a flow diagram of an embodiment of a method 400 for detecting and monitoring electrical current 350 flow through a cured bondline 32 of a structural assembly 34. Step 402 of the method 400 may include passing an electrical current 350 through an adhesive layer 52 of a cured bondline 32 of the structural assembly 34. As indicated above, the electrical current 350 may have a magnetic field 352 associated therewith. The electrical current 350 may be a relatively high-intensity transient electrical current or pulse passing through the cured bondline 32. In some examples, the high-intensity transient electrical current or pulse may be the result of a lightning strike on an aircraft containing the structural assembly 34. The structural assembly 34 may include a cured bondline 32 containing an adhesive layer 52 within which a current sensor network 302 may be embedded. As indicated above, the current sensor network 302 may include a plurality of inductive coils 304 electrically interconnected at a plurality of current sensor nodes 330 and forming a plurality of current sensor loops 338.

Step 404 of the method 400 may include inducing an induced current 306 in the current sensor loops 338 in response to the magnetic field 352 associated with the electrical current 350 passing through the cured bondline 32. As indicated above, the magnetic field 352 may induce a relatively low-amperage induced current 306 in one or more of the inductive coils 304 of the current sensor network 302. As mentioned above, the inductive coils 304 may have a relatively low profile or height so that the inductive coils 304 may fit within a relatively thin bondline associated with adhesively-bonded joints 33. In this regard, the inductive coils 304 may be provided with a generally flattened cross-sectional shape 318 in order to increase the area of the inductive profile, and thereby may enhance the ability of the inductive coils 304 to pick up the magnetic field 352 such that an induced current 306 may be generated in the inductive coils 304.

Step 406 of the method 400 may include generating, at the current sensor nodes 330, current signals 344 representative of the induced current 306. In some examples, one or more of the current sensor nodes 330 may include electronic circuitry or logic for converting the induced current 306 into current signals 344. A current signal 344 generated by a current sensor node 330 may be proportional to or representative of the induced current 306 in the inductive coils 304. For example, a current signal 344 may represent the amperage of the induced current 306 in the inductive coil 304 that terminates at the current sensor node 330.

Step 408 of the method 400 may include transmitting one or more of the current signals 344 to a digital data communications network 76 which may be located external to the cured bondline 32. In this regard, the current sensor nodes 330 may be electrically connected to one or more current integrators 346 associated with a data retrieval system 78 of the digital data communications network 76. In some examples, each one of the current sensor nodes 330 may be electrically connected via a signal wire 342 to a dedicated current integrator 346 which may be located external to the cured bondline 32. However, in some examples, the current integrators 346 may be incorporated into the current sensor nodes 330, and the signal wires 342 may transmit current signals 344 from the current sensor nodes 330 to a data processing system 80 of the digital data communications network 76.

Step 410 of the method 400 may include detecting and monitoring the electrical current 350 using the digital data communications network 76 based on the current signals 344. As indicated above, the digital data communications network 76 may be configured to detect the presence of an electrical current 350 passing through the cured bondline 32. For example, the digital data communications network 76 may compare the summed total of the magnitude of the individual current signals 344 to a predetermined baseline or threshold current value. When the summed total of the individual currents exceeds the threshold current value, the digital data communications network 76 may indicate in real time or recorded time that an electrical current 350 is passing through or has passed through one or more portions of the cured bondline 32. In some examples, a current profile of the electrical current 350 may be displayed or plotted on an oscilloscope (e.g., plotting plot the amperage over time) as may be included with the digital data communications network 76.

In some examples, the method may include determining a relative magnitude of the electrical current 350 passing through the adhesive layer 52 at locations adjacent to the current sensor nodes 330 based upon the relative magnitude of the current signals transmitted from each current sensor node 330. In another example, the method may include summing the output signals 348 generated by each one of the current integrators 346, and determining the total electrical charge passing through the cured bondline 32 during an electrical current 350 event (e.g., during an actual or simulated lightning strike) based on the output signals 348. In this manner, the current sensor network 302 may provide a means for determining the severity of a lightning strike in terms of absolute magnitude and/or relative magnitude of the total electric charge associate with the electrical current 350. Based upon the magnitude of the total electric charge measured at the bonded joint 33, a determination may be made regarding whether inspection of the bonded joint 33 is necessary.

In some examples, the method may include determining the electrical current 350 passing through one or more bonded joints 33 of a vehicle such as an aircraft 10. In this regard, the method may include providing certain bonded joints 33 with a current sensor network 302 in the cured bondline 32. Each one of the current sensor networks 302 may be electrically connected to a digital data communications network 76 and/or to an IVHM system 124. The bonded joints 33 may be monitored with a time stamp to enable the determination of flow direction and/or direction of propagation of an electrical charge as it passes through a structure such as through an aircraft subjected to a lighting strike or other high-intensity electrical charge. Determining the flow path of electrical charge through a structure such as an aircraft may assist in identifying a location of the lightning strike on the aircraft and identifying the bonded joints 33 that were subjected to high-intensity electrical current 350 associated with the lightning strike. A similar current detection system 300 and method may be incorporated into any type of structure, without limitation, including any type of vehicular or non-vehicular structure.

B. Lightning Damage Index

FIG. 17 shows an example of an index 1700 that compiles data generated for various types of aircraft and provides numeric representations for predicted lightning strike damage to the various types of aircraft. The lightning strike damage takes into account the likelihood of a lightning strike to the respective aircraft and the area of the aircraft that lightning may strike, which can have a significant impact on the extent of damage. The numeric representations are based on the compiled generated data for the respective types of aircraft. The types of aircraft featured in the index may be selected as desired and based on user criteria. In this example, the aircraft listing is selected based on general features such as hauling distance, engine type, and body type. In other embodiments, the aircraft selected for listing may be based on a specific engine, basis of use (commercial or private), purchasing sector (military or civilian), manufacturer, year produced, or other categories. The number of aircraft selected for the index may range from one to any desired number.

Figure 18:
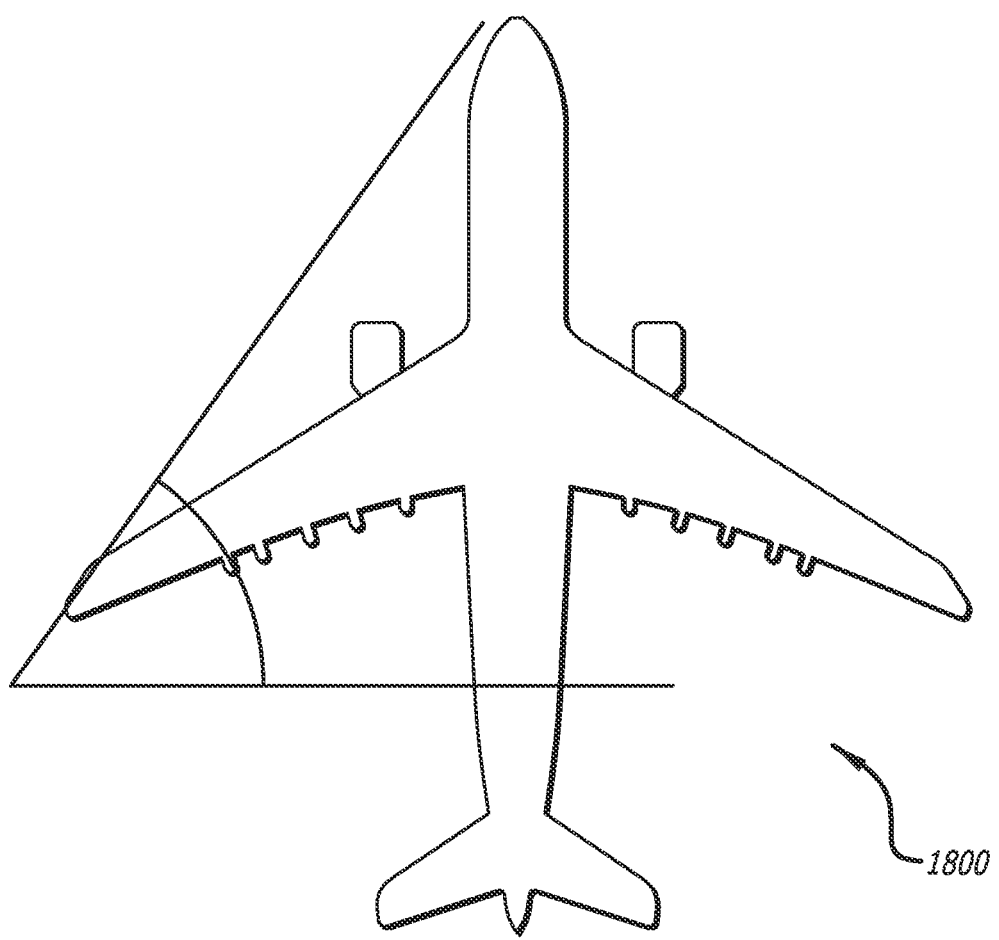
FIG. 18 shows a geometric representation for determining a nose to wing angle on an aircraft.

In providing the generated data, the index 1700 features dimensional measurements of each aircraft type. This may be used to evaluate and present additional data in the index relating to lightning strike damage to each type of aircraft. In the illustrated embodiment, a measurement of the dimensions of a particular aircraft type provides the nose to wing root angle of the aircraft, which may affect lightning strike damage to the aircraft. A geometric illustration 1800 of the nose to wing root angle of an aircraft is shown in FIG. 18. In other embodiments, other aspects of measurements of each aircraft type may be included, such as radome dimensions, wingspan, tail height relative to the nose, and other dimensional features.

Other data in index 1700 includes design features that are assessed for each type of aircraft. In the illustrated embodiment, winglet inclusion is a specified design feature, and the index 1700 features multiple rows for each type of aircraft to reflect the presence or absence of a winglet, for easier use of the index 1700. Radome design for each type of aircraft is also included based on the potential impact of the radome design on lightning strike frequency and lightning strike location on the aircraft. To further illustrate, FIG. 17 shows sample radome curve designs with index 1700 featuring width-to-height (W/H) ratios and a scale of low, medium, and high curvature corresponding to the ratios. The scale is incorporated in the index 1700 for reference in selecting the appropriate design of the aircraft. In the present embodiment, other features of the radome design are also included, namely, radome material and the presence of supplemental protection. In other embodiments, other design features having a potential impact on lightning strike frequency and lightning strike location on the aircraft may be included, such as engine location, wing design, and aircraft body materials.

Additional data in index 1700 includes the electromagnetic densities associated with different areas of the aircraft. The electromagnetic density for a particular area of the aircraft may impact the extent of lightning strike damage to that particular area and/or to the aircraft as a whole. In the illustrated embodiment, the index 1700 includes electromagnetic densities associated with the aircraft nose in kilovolts/meter (kV/m). In alternative embodiments, the electromagnetic density may be featured in other units and/or for other areas of the aircraft.

Following the generated data, index 1700 provides the numeric representation for predicted lightning strike damage for each type of aircraft. In the illustrated embodiment, the index 1700 provides a numeric representation in the form of a probability expressed as a percentage for predicting a lightning strike to each aircraft type and at a particular location on the aircraft, which is the nose in the present embodiment, wherein a higher percentage represents a higher likelihood of a lightning strike to the nose of the aircraft. In alternative embodiments, other numeric representations may be utilized such as: a scale of 1 to 10, with 1 representing a low likelihood and 10 representing a high likelihood of a lightning strike; or a positive and negative scale, with 0 representing normal likelihood of a lightning strike, positive integers representing a higher likelihood, and negative integers representing a lower likelihood (or vice-versa). Also in the illustrated embodiment, the numeric representation for a predicted lightning strike is directed to a specific location on the aircraft. In alternative embodiments, numeric representations for predicted lightning strikes to other parts of the aircraft, such as wings and/or the tail, may also be provided, or the numeric representation may not be limited to a particular location on the aircraft.

The numeric representation may be based upon: an algorithmic relationship derived between the listed features for each aircraft design; empirical data gathered in the course of operation; or a combination of an algorithmic relationship and empirical data. As an example, each particular aircraft design may have a higher or lower likelihood of incurring lightning strikes based on known lightning strike frequency and lightning strike location for that design. For example, in generating the data for the index, operational data may be gathered to show that one type of aircraft incurs a lightning strike on the nose once every 50 flights, while another type of aircraft incurs a lightning strike on the nose once every 100 flights.

The other data presented in the index 1700, such as the dimensions and design features of the aircraft, may also serve to modify the numeric representation. For example, operational data may be gathered to indicate that the presence of a winglet increases the likelihood of a lightning strike on the nose by 15%. As another example, operational data may be gathered to indicate that the a 45° nose to wing root angle has no impact on lightning strike frequency and/or damage incurred, while a 30° nose to wing root angle corresponds to a 20% increase in lightning strike frequency with severe damage to the nose. The lightning strike data associated with these probabilities may be tabulated based on an algorithmic relationship (e.g., addition, multiplication) to create a final probability for a lightning strike on the nose, which is presented in the index. In other embodiments, probabilities for a lightning strike on other aircraft locations, such as the wings, may be included.

In an alternative embodiment, each feature in the index 1700 may be assigned a numerical value. For example, each aircraft design may be assigned a numerical value based on lightning strike history for the respective design. The design features in the index may also be assigned numerical values based on the known impact of the features on lightning strikes. For example, a winglet for a particular aircraft design may have a value of +3 for increasing the likelihood of a lightning strike on the nose, while a wing to root ratio of 30° for a particular aircraft design may have a value of +5 for also increasing the likelihood of a lightning strike on the nose, such that these become additive effects for determining the numeric representation associated with predicted lightning strike damage, which may be represented as a Lightning Damage Index (LDI).

The numeric representation for predicted lightning strike damage to the aircraft may also be modified by several factors relating to the aircraft. These factors may be operational in nature, such as departure frequency, flight altitude, geographic region in which the aircraft operates, and a selected time period during which the aircraft operates. Data relating to these factors may be generated as appropriate for a user. The combined result of the numeric representation and the modifying factors may be represented collectively in the LDI. As examples of the factors, departure frequency may be provided on a flights per week basis. Geographic location may be provided as countries, navigational coordinates, or user-delineated areas. Altitude may be provided as a general altitude at which an aircraft spends most operating time, or more specifically as a frequency of a specific altitude within a constant time at which an aircraft operates. Time period may be provided as a seasonal period, a calendar period, or any other desired time period. The time period may also be adjustable to reflect specific time periods as needed.

To further illustrate use of the factors in the index 1700, first referring to altitude, the index 1700 shows three different altitudes for each aircraft type. As examples, altitudes of 8,000 feet (ft), 10,000 ft, and 12,000 ft are provided, but the displayed altitudes may vary as desired. The index 1700 also shows the change in lightning strike probability at each altitude for the respective aircraft type.

Figure 20:
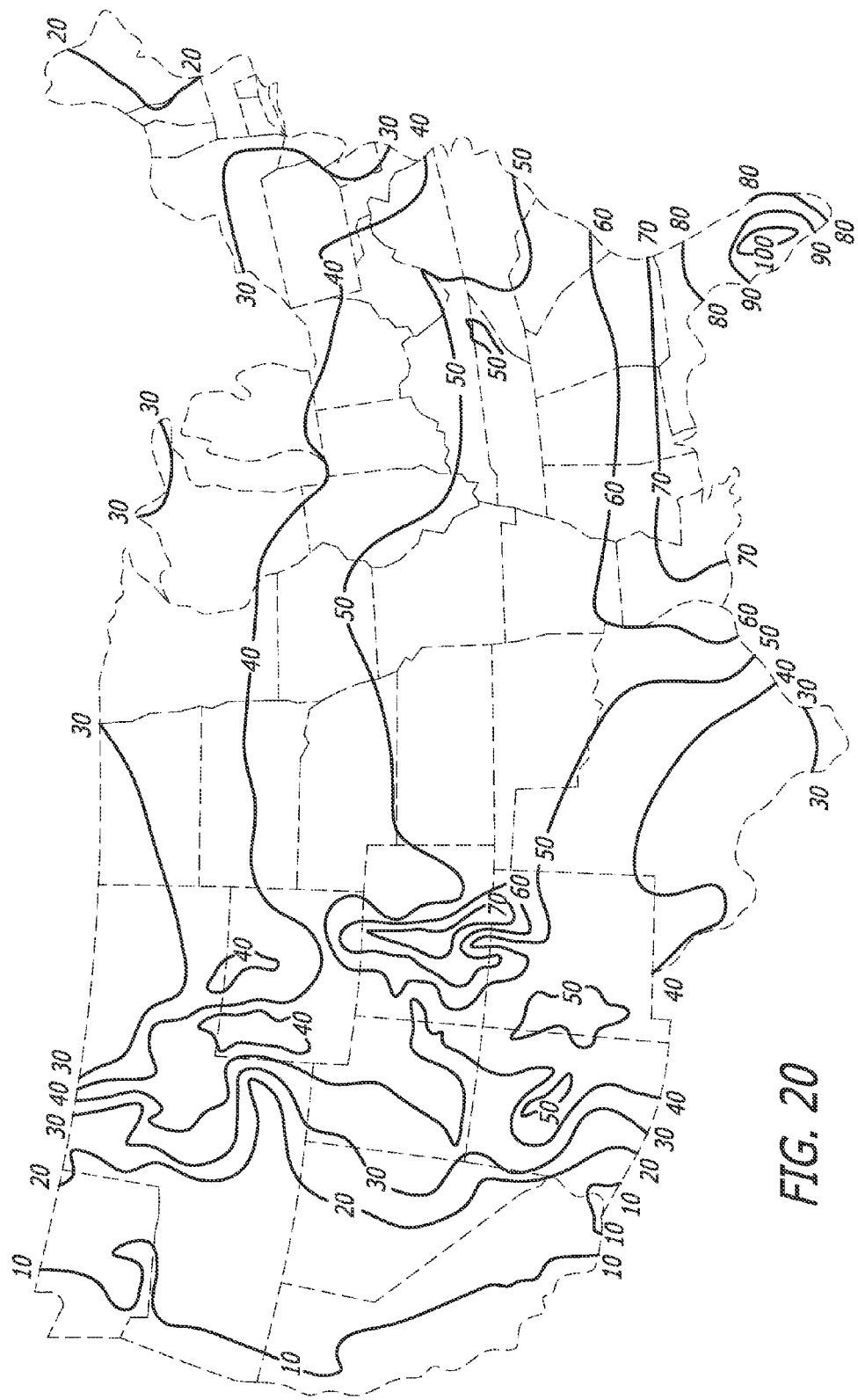
FIG. 20 shows a representative data sampling of thunderstorm days over a geographic area.

Referring to geographic area, the index 1700 shows lightning strike days per year for a geographic area and the change in lightning strike probability for aircraft operating in that geographic area. As a base reference, FIG. 20 provides a map showing regions of the U.S. and the number of thunderstorm days per year for those regions in the range of 1 to 100 days. As illustrative examples, Oklahoma has 50 thunderstorm days per year and the west coast of California has 10 thunderstorm days per year. The index 1700 shows such representative thunderstorm days and the change in lightning strike probability. In this embodiment, geographic regions with 0-20 thunderstorm days are considered as having a low lightning strike level, so that lightning strike probability is only increased by 2%. Geographic regions with 20-80 thunderstorm days have a medium lightning strike level and increase strike probability by 5%, and geographic regions with 80-100 thunderstorm days have a high lightning strike level and increase strike probability by 10%.

Referring to time period, the index 1700 in the illustrated embodiment features a seasonal time period, namely storm season. Here, the index 1700 shows the increase in lightning strike probability if an aircraft operates during storm season, wherein there is a 20% increase in lightning strike probability if an aircraft operates during storm season. Other time periods may also be featured, such as calendar time periods or specific operating time periods selected by a user. Multiple time periods may also be included, such that a user may plan for a range of operating times in considering the possibility of lightning strikes on aircraft.

By applying factors that modify the numeric representation, a user may take into consideration conditions that are specific to a particular aircraft to more accurately predict lightning strike damage to that aircraft. For example, a plane that flies in a particular geographic region with inclement weather patterns may be more likely to incur a lightning strike with greater damage than an aircraft that flies in a region with more favorable weather for operation. In this manner, an aircraft operator can plan for certain types of aircraft to have greater availability and require less repair materials and staffing, while at the same time planning for other aircraft to be less available and to have repair materials and crews available for that type of aircraft due to the possibility of lightning strike damage.

In the illustrated embodiment, the factors have a numerical value for modifying the numeric representation of the predicted lightning strike. In particular, the factors may have a numerical value that is consistent with the numeric representation. For example, if the numeric representation for predicted lightning strike damage is expressed as a probability, the numerical values of the factors may also be expressed as a probability. To further illustrate, the index may show that one aircraft type has a 5% probability of incurring lightning strike damage to the nose. However, the geographic region in which a user assigns that aircraft type to operate may have a high frequency of lightning storms, such that the geographic region corresponds with a threefold increase in probability of incurring lightning strike damage to the nose for that type of aircraft. In a further embodiment, there is an algorithmic association between the numeric representation and the factors. In one embodiment, the numeric representation for predicting a lightning strike is presented as a probability, and each factor has a numeric value that is multiplied with the probability.

To expand upon the example above, the 5% probability of incurring lightning strike damage to the nose is multiplied by 3 based on the threefold increase in the probability due to the geographic region, resulting in a 15% probability of incurring lightning strike damage to the nose. In another embodiment, the numerical representation may be totaled with the numeric value of the factors.

To further illustrate, an algorithmic association between the numeric representation and the factors can be represented by the following equation, in which the numeric representation and the factors are represented by probabilities that are multiplied to predict lightning strike damage as represented by the Lightning Damage Index:

$$LDI = NR \times FA \times DF \times GR \times TP$$

wherein LDI=Lightning Damage Index, NR=numeric representation, FA=probability of a lightning strike based on flight altitude, DP=probability of a lightning strike based on departure frequency, GR=probability of a lightning strike based on the geographic region of operation, and TP=time period. In another embodiment, the LDI may be determined from an addition algorithm wherein the numeric representation and the factors are represented by probabilities that are added, such as:

$$LDI = NR + FA + DF + GR + TP$$

In yet another embodiment, the LDI may be determined from an algorithm combining functions, such as:

$$LDI = NR \times FA \times DF \times GR + TP.$$

Other examples of algorithmic relationships may be applied that are suited for predicting lightning strike damage.

In another alternative embodiment, the factors may not have a numerical value but instead may be assigned qualitative representations. For example, an aircraft that has approximately 1200 or more departures a year may have a high likelihood of incurring lightning strike damage, such that a departure frequency range of 1200-1500 departures per year may indicate "very high risk." On the other hand, an aircraft that only has approximately 300 departures a year may have a low likelihood of incurring lightning strike damage, such that a departure frequency range of 200-300 departures per year may indicate "low risk." In this manner, a user may refer to the numeric representation for a predicted lightning strike, and then note that the numeric representation may be modified based on the qualitative data associated with the respective factors.

In another embodiment, one or more impact levels that is respectively associated with one or more of the aircraft type, the data associated with the aircraft, and the factors is applied to modify one or both of the numeric representation for predicting lightning strike damage to the aircraft and the associated factors (e.g., flight altitude). The purpose of applying the impact level is to account for additional considerations for predicting lightning strike damage. To illustrate, considering the factors of altitude and time period, if a particular aircraft flies at a high-risk altitude for a lightning strike during only half of the selected time period, the weight of altitude in predicting lightning strike damage may be reduced. Thus, the impact level associated with altitude may be assigned a numeric value, such as −50%, that is applied in an algorithmic relationship to the respective factor. To illustrate, expanding on one of the example algorithmic relationships represented by the equations above, the impact levels may be incorporated with the factors as follows:

$$LDI = NR \times K_1 FA \times K_2 DF \times K_3 GR \times K_4 TP$$

wherein $K_1$=the impact level associated with flight altitude, $K_2$=the impact level associated with departure frequency, $K_3$=the impact level associated with geographic region, and $K_4$=the impact level associated with time period. The impact levels may be: constants based on empirical data or other information; variables based on data and/or functions; or both. To provide other examples, in one embodiment, the impact levels are assigned values such that the impact levels have a total value of one. In another embodiment, the impact levels are integers with values based on empirical data.

In an alternative embodiment, the impact level may be expressed qualitatively, such as in "decreased risk." In one embodiment, the impact levels are presented in a table to associate the respective aircraft, generated data, and modifying factors with the appropriate impact level. The impact levels may be derived from operational data, scientific research, or other sources.

By using the system with index featuring the numeric representation for predicted lightning strike damage, the modifying factors, and the impact levels, a user may prepare for lightning strike damage to an aircraft while considering the conditions under which the aircraft operates. For example, if a certain aircraft is known to fly a route at an altitude at which lightning strike damage is expected to increase, the operator can have maintenance crews and materials ready at the aircraft destination points for any necessary repairs. The operator may also plan to have additional aircraft available for flying that specific route, should lightning strike damage remove other aircraft from operation. An aircraft operator can also refer to the index to select aircraft that is less likely to incur lightning strike damage in order to select aircraft with a low propensity for incurring lightning strike damage to fly in conditions with elevated lightning activity, e.g., certain geographic areas or during specific time periods. Likewise, an aircraft operator can select aircraft with a high propensity for incurring lightning strike damage to fly in conditions with low lightning activity. As such, a user can use the data as needed and has a wide range of optional considerations in predicting lightning strike damage to an aircraft and thus optimizing the aircraft equipment selection and configuration using particular LDI for the operating equipment design and conditions.

In one embodiment, a computer processor is used (e.g., by running a lightning damage index application or algorithm) to generate the index 1700 and the selected factors and impact levels. As an example, a user may access the computer processor and command the processor to generate the index 1700. The user may input data as desired in the index 1700, wherein the computer processor includes a database for accessing data associated with the user inputs, e.g., numerical values associated with lightning strike damage for aircraft design features, such as winglets and with the factors, such as altitude and geographic area. The computer processor then processes the inputs to complete the index and provide a numeric representation associated with the aircraft type, as well as the LDI that is based on any selected factors and associated impact levels. In this manner, the user may manipulate inputs to obtain various predictions for lightning strike damage and subsequently plan operations based on the information generated from the computer processor through the index 1700.

Figure 19:
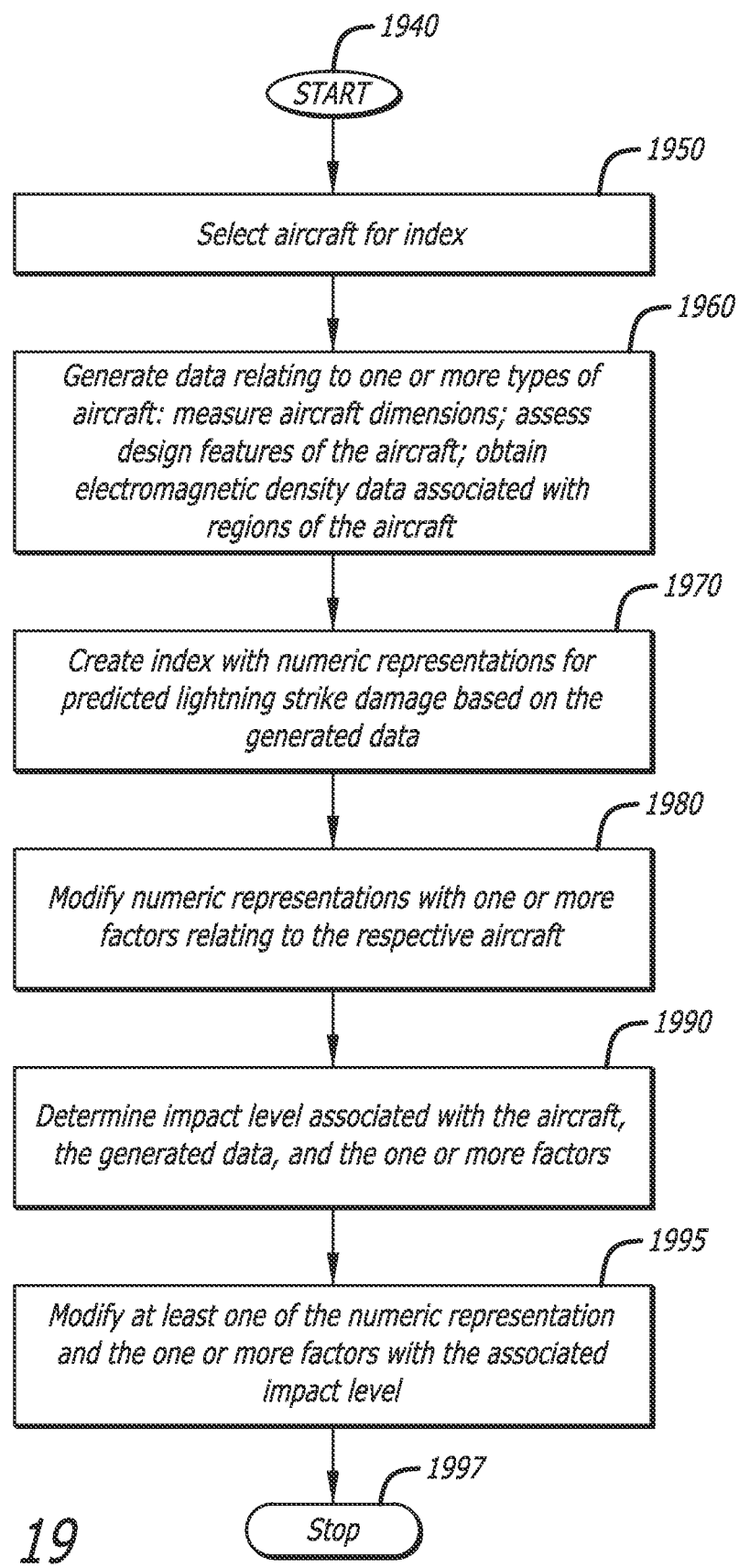
FIG. 19 shows a method of creating an embodiment of the index of FIG. 17.

Having described a system for predicting lightning strike damage to one or more types of aircraft, a method of predicting lightning strike damage to one or more types of aircraft will now be described. Referring to FIG. 19, the method is started (step 1940) by selecting one or more types of aircraft for which lightning strike damage is to be predicted are selected (step 1950). Data relating to the aircraft is then generated by measuring the dimensions of the aircraft, assessing the design features of the one or more types of aircraft (e.g., winglets), and obtaining electromagnetic density data associated with regions of the one or more types of aircraft (step 1960). An index is then created that provides a numeric representation for predicted lightning strike damage to the one or more types of aircraft based on the generated data (step 1970). The numeric representation may be directed to predicting lightning strike damage to a specific location on the aircraft.

In one embodiment, the numeric representation may also be modified with one or more factors relating to the aircraft, such as departure frequency, geographic region of operation, flight altitude, and/or time period of operation (step 1980). The factors may be assigned numeric values, which may further have an algorithmic relationship with the numeric representation for predicting lightning strike damage. Alternatively, the factors may be expressed qualitatively (i.e., "high risk" or "low risk"). In a further embodiment, an impact level is determined that is associated with one or more of the aircraft, the generated data, and the modifying factors (step 1990). The impact level may be obtained from a table that displays each impact level associated with the respective aircraft, generated data, and modifying factors. The impact level may then be used to modify one or both of the numeric representation and the factors (step 1995). The method may then be completed (step 1997).

Figure 21:
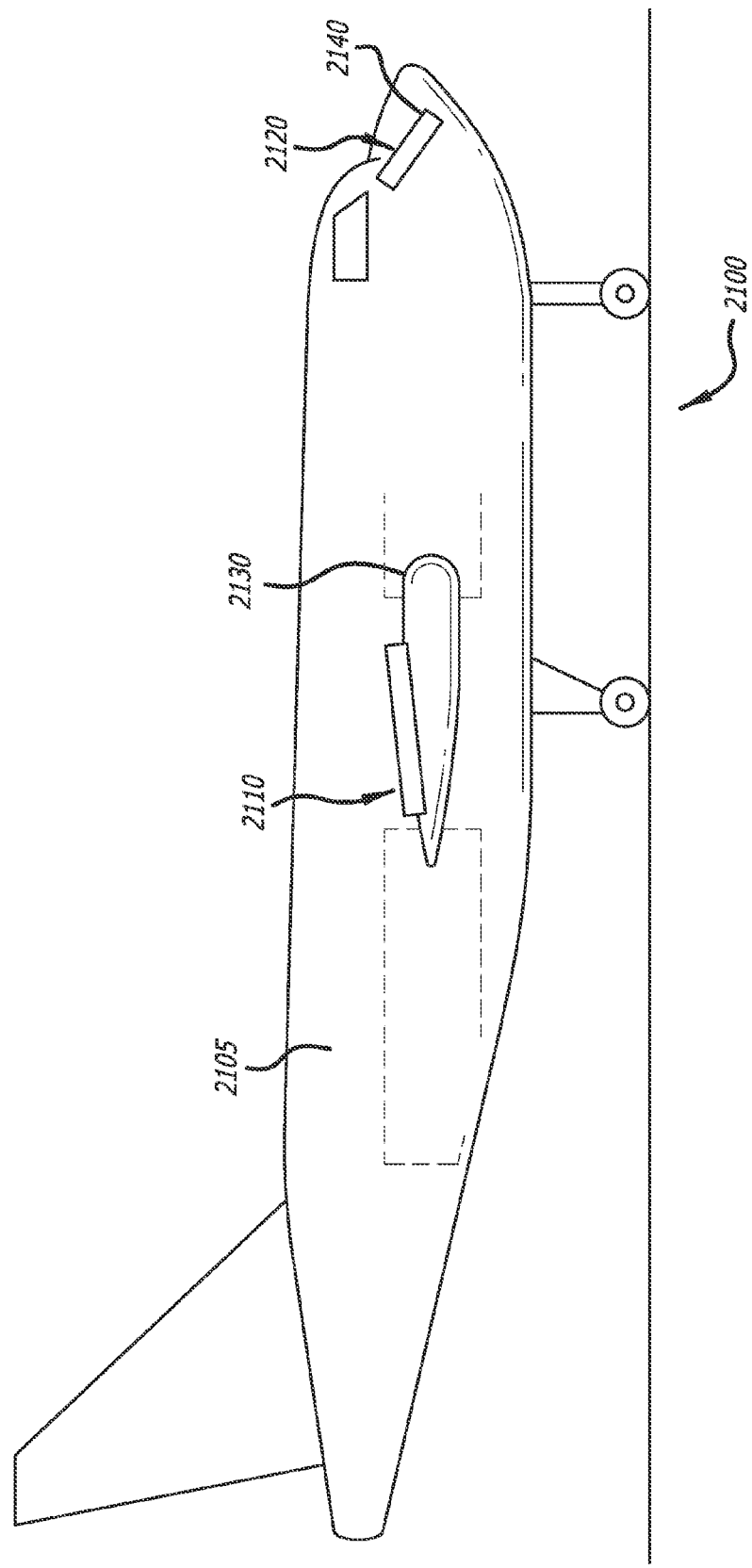
FIG. 21 is a diagram illustrating the disclosed system for utilization of aircraft bondline embedded current sensors in the determination of a lightning damage index, in accordance with at least one embodiment of the present disclosure.

C. Utilization of Aircraft Bondline Embedded Current Sensors in the Determination of a Lightning Damage Index FIG. 21 is a diagram 2100 illustrating the disclosed system for utilization of aircraft bondline embedded current sensors in the determination of a lightning damage index (LDI), in accordance with at least one embodiment of the present disclosure. In this figure, two cured bondlines 2110, 2120 are shown to be embedded into an aircraft 2105. Specifically, one cured bondline 2110 is shown to be embedded into a wing region 2130 of the aircraft 2105, and the other cured bondline 2120 is shown to be embedded into the cockpit region 2140 of the aircraft 2105. In one or more embodiments, the cured bondline 32 (e.g., refer to FIGS. 2, 3, and 11) as described in the Bondline Embedded Current Sensor section of the present disclosure may be employed for the cured bondlines 2110, 2120. For these embodiments, each cured bondline 2110, 2120 comprises current sensor nodes that provide sensed current information. For monitoring of the aircraft 2105 during flight, the current sensor nodes can provide the sensed current information real time during flight.

The sensed current information can be used in determining a LDI for the specific region of the aircraft 2105 that the cured bondline 2110, 2120 is located. For example, a LDI can be determined for the wing region 2130 of the aircraft 2105 by using sensed current information from cured bondline 2110. The LDI can be used to indicate whether any delamination may have occurred in the wing region 2130 of the aircraft 2105, which may have occurred as a result of a lightning strike. Similarly, for example, a LDI can be determined for the cockpit region 2140 of the aircraft 2105 by using sensed current information from cured bondline 2120. The LDI can be used to indicate the amount of damage caused by electric field exposure that has occurred to the cockpit instruments in the cockpit region 2140 of the aircraft 2105, which may have occurred as a result of a lightning strike.

Referring back to FIG. 11, FIG. 11 shows an illustration of an exemplary cured bondline 32 that may be employed for the cured bondlines 2110, 2120 of the disclosed system of FIG. 21. As previously mentioned above, in particular, FIG. 11 is an illustration of a partial cross-sectional view of a structural assembly showing an embodiment of a current sensor network embedded in an adhesive layer of a bonded joint joining the first and second structure of the structural assembly. Specifically, FIG. 11 shows a cross-sectional view of a structural assembly 34 of a first structure 36 adhesively bonded to a second structure 42 at a bonded joint 33. The bonded joint 33 includes a cured bondline 32 contain adhesive bonding the first faying surface 37 of the first structure 36 to the second faying surface 43 of the second structure 42. The cured bondline 32 includes a current sensor network 302 embedded in the adhesive layer 52 of the bonded joint 33. The current sensor network 302 includes a plurality of inductive coils 304 embedded in the adhesive layer 52 and electrically interconnected to one another by a plurality of current sensor nodes 330. Each one of the inductive coils 304 has a lengthwise direction oriented generally parallel to the first and second faying surfaces 37, 43 of the first and second structure 36, 42.

During operation for the determining of an LDI for a region of the aircraft 2105, the dimensions of the aircraft 2105 are determined by measuring the dimensions of the aircraft 2105 or by measuring the dimensions of a different aircraft of the same type of aircraft 2105. Also, the design features (e.g., winglets) of the aircraft 2105 are determined by assessing the design features of the aircraft 2105 or by assessing the design features a different aircraft of the same type of aircraft 2105.

Then, on the ground or during flight for real time monitoring of the aircraft 2015, an electrical current 350 (refer to FIG. 11) passes through the adhesive layer 52 along a direction from the first structure 36 to the second structure 42. However, it should be noted that, the electrical current 350 may pass through the adhesive layer 52 along a direction from the second structure 42 to the first structure 36. The electrical current 350 may be generated by a power source (e.g., wireless electrical power source 116 of FIG. 8) when, for example, the aircraft 2105 is on the ground. Or, the electrical current 350 may be generated by an electromagnetic field generated (e.g., by a lightning strike) when, for example, the aircraft 2015 is in flight. In addition, the electrical current 350 may be generated by an electromagnetic field generated (e.g., by an electric field generator) when, for example, the aircraft 2015 is on the ground during test.

A magnetic field 352 may be associated with the electrical current 350 passing through the adhesive layer 52. The magnetic field 352 may induce an induced current 306 in the inductive coils 304 which may be picked up at (or sensed by) the current sensor nodes 330. The current sensor nodes 330 may generate current signals 344 (refer to FIG. 12) representative of the induced current 306. The current signals 344 may be transmitted via signal wires 342 (refer to FIG. 12) to, for example, the digital data communications network 76 as shown in FIG. 1.

After the current signals 344 are obtained, electromagnetic density data is determined (e.g., by at least one computer processor, which may be, for example, in the data processing system 80 of FIG. 2 and/or in the wireless data processing system 122 of FIG. 3) from the current signals 344. The electromagnetic density data can be determined by utilizing calibration data from calibration of the current sensor nodes 330 while the aircraft 2105 is on the ground during test. During the calibration of the current sensor nodes 330, a known electric field is applied to the current sensor nodes 330. Calibration current signals generated from the current sensor nodes 330 during calibration are obtained. These calibration current signals (e.g., the calibration data) can be compared (e.g., by at least one computer processor) with the obtained current signals 344 to determine the electromagnetic density data.

After the electromagnetic density data is determined, the LDI is created that provides a numeric representation for predicted lightning strike damage to a region (e.g., the wing region 2130 or the cockpit region 2140) of the aircraft 2105 based on the electromagnetic density data, the dimensions of the aircraft 2105, and the design features of the aircraft 2105. Refer to the Lightning Damage Index section of the present disclosure for additional details regarding the creation of the LDI.

Figure 22:
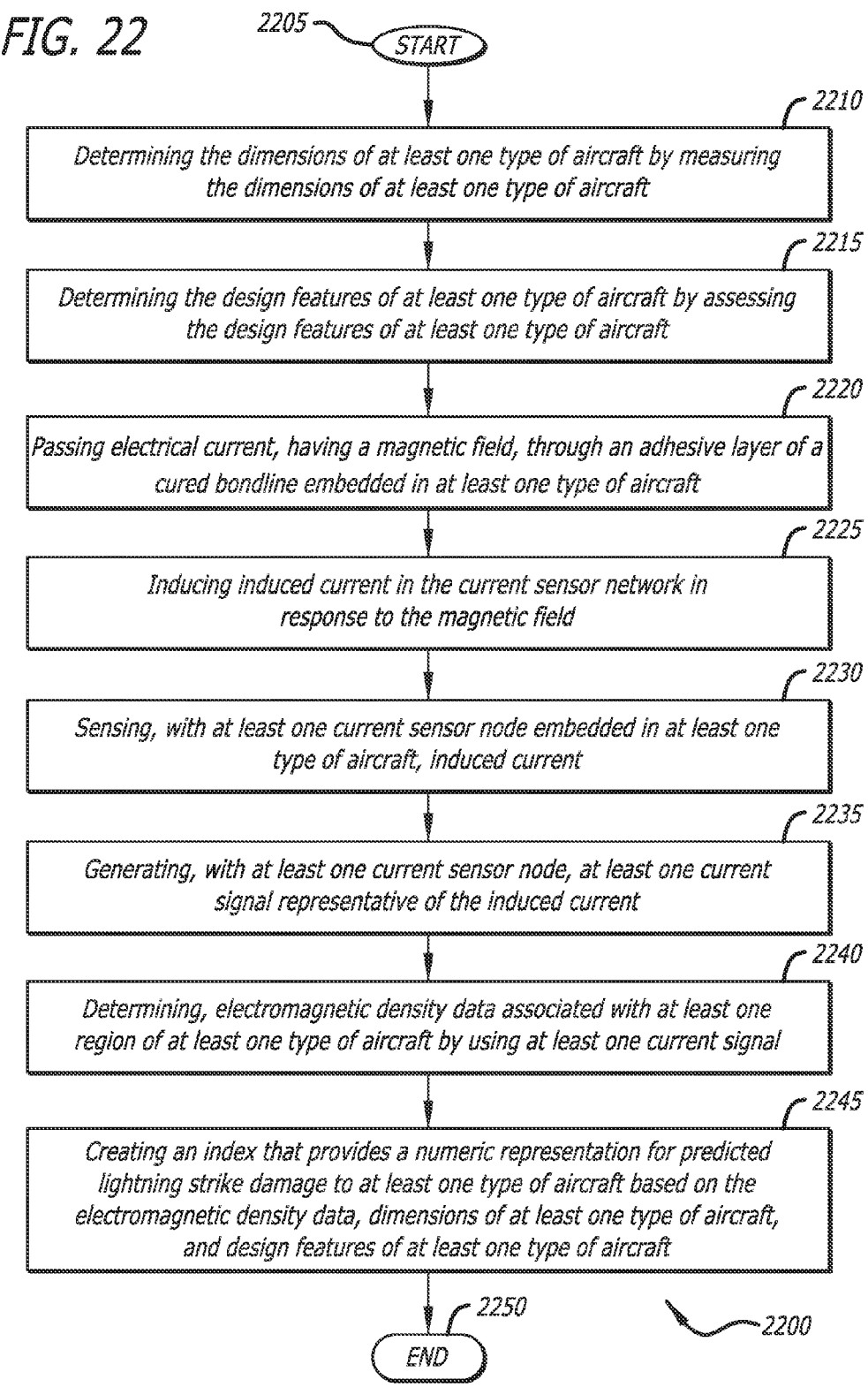
FIG. 22 is a flow chart depicting the disclosed method of utilization of aircraft bondline embedded current sensors in the determination of a lightning damage index, in accordance with at least one embodiment of the present disclosure.

FIG. 22 is a flow chart depicting the disclosed method 2200 of utilization of aircraft bondline embedded current sensors in the determination of a lightning damage index, in accordance with at least one embodiment of the present disclosure. At the start 2205 of the method 2200, the dimensions of at least one type of aircraft are determined by measuring the dimensions of at least one type of aircraft (step 2210). Also, the design features of at least one type of aircraft are determined by assessing the design features of at least one type of aircraft (step 2215).

Then, electrical current, having a magnetic field, is passed through an adhesive layer of a cured bondline embedded in at least one type of aircraft (step 2220). In one or more embodiments, a current sensor network is embedded in the adhesive layer. In at least one embodiment, the current sensor network comprises at least one current sensor node. Induced current is induced in the current sensor network in response to the magnetic field (step 2225). At least one current sensor node senses the induced current (step 2230). At least one current sensor node generates at least one current signal representative of the induced current (step 2235).

At least one processor determines electromagnetic density data associated with at least one region of at least one type of aircraft by using at least one current signal (step 2240). Then, at least one processor creates an index that provides a numeric representation for predicted lightning strike damage to at least one type of aircraft based on the electromagnetic density data, the dimensions of at least one type of aircraft, and the design features of at least one type of aircraft (step 2245). Then, the method 2200 ends 2250.

Figure 23:
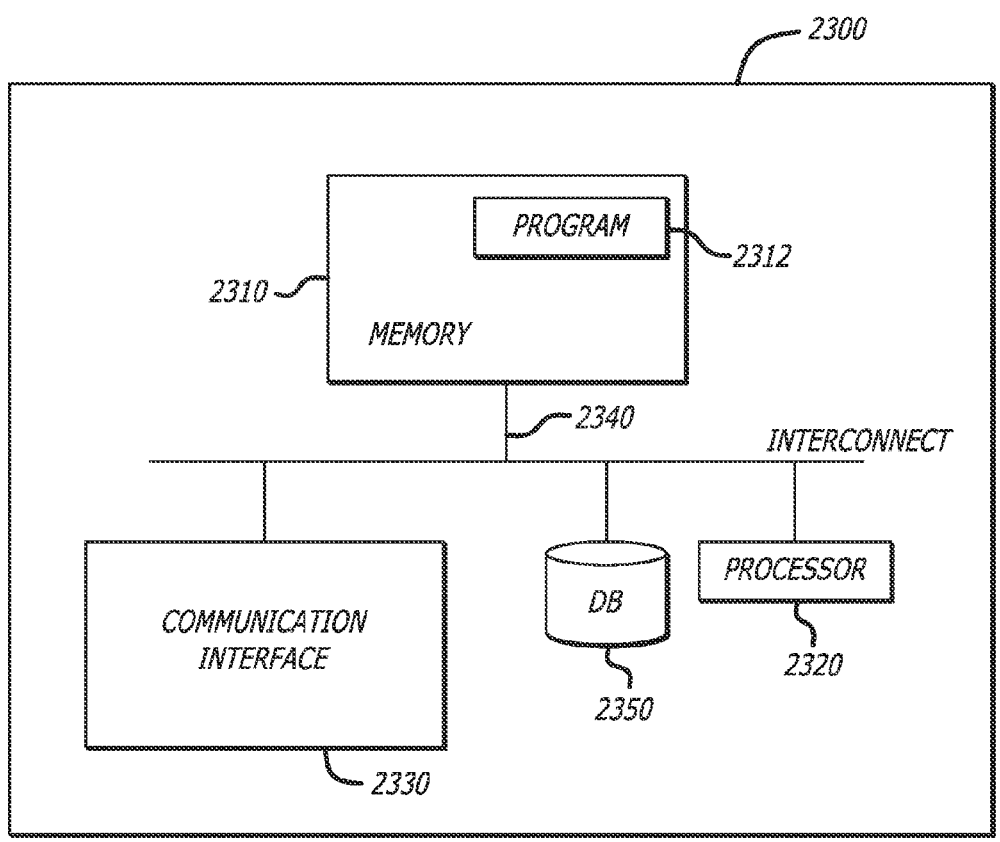
FIG. 23 is a block diagram of components of a computing apparatus or system in which various embodiments may be implemented or that may be utilized to execute embodiments.

FIG. 23 is a block diagram 2300 of components of a computing apparatus or system in which various embodiments may be implemented or that may be utilized to execute embodiments. FIG. 23 generally illustrates components of a computing device 2300 that may be utilized to execute embodiments and that includes a memory 2310, a program (e.g., lightning damage index application instructions) 2312, a processor or controller (e.g., a computer processor) 2320 to execute the program 2312, a database 2350 for storing data, a network interface 2330, e.g., for communications with a network or interconnect 2340 between such components. The memory 2310 may be or include one or more of cache, RAM, ROM, SRAM, DRAM, RDRAM, EEPROM and other types of volatile or non-volatile memory capable of storing data. The processor unit 2320 may be or include multiple processors, a single threaded processor, a multi-threaded processor, a multi-core processor, or other type of processor capable of processing data. Depending on the particular system component (e.g., whether the component is a computer or a hand held mobile communications device), the interconnect 2340 may include a system bus, LDT, PCI, ISA, or other types of buses, and the communications or network interface may, for example, be an Ethernet interface, a Frame Relay interface, or other interface. The network interface 2330 may be configured to enable a system component to communicate with other system components across a network that may be a wireless or various other networks. It should be noted that one or more components of computing device 2300 may be located remotely and accessed via a network. Accordingly, the system configuration provided in FIG. 23 is provided to generally illustrate how embodiments may be configured and implemented.

Method embodiments may also be embodied in, or readable from, a computer-readable medium or carrier, e.g., one or more of the fixed and/or removable data storage data devices and/or data communications devices connected to a computer. Carriers may be, for example, magnetic storage medium, optical storage medium and magneto-optical storage medium. Examples of carriers include, but are not limited to, a floppy diskette, a memory stick or a flash drive, CD-R, CD-RW, CD-ROM, DVD-R, DVD-RW, or other carrier now known or later developed capable of storing data. The processor 2320 executes program instructions 2312 within memory 2310 and/or embodied on the carrier to implement method embodiments. Further, embodiments may reside and/or execute on a mobile communication device such as a cellular telephone or Smartphone.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims.

As a further example, embodiments may involve a lightning damage index application or algorithm (which may be run on at least one computer processor) that is a stand alone application, which may contain one or more programs, or that is part of another system or program.

Although particular embodiments have been shown and described, it should be understood that the above discussion is not intended to limit the scope of these embodiments. While embodiments and variations of the many aspects of the present disclosure have been disclosed and described herein, such disclosure is provided for purposes of explanation and illustration only. Thus, various changes and modifications may be made without departing from the scope of the claims.

Where methods described above indicate certain events occurring in certain order, those of ordinary skill in the art having the benefit of this disclosure would recognize that the ordering may be modified and that such modifications are in accordance with the variations of the present disclosure. Additionally, parts of methods may be performed concurrently in a parallel process when possible, as well as performed sequentially. In addition, more parts or less part of the methods may be performed.

Accordingly, embodiments are intended to exemplify alternatives, modifications, and equivalents that may fall within the scope of the claims.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A method of predicting lightning strike damage to at least one type of aircraft, the method comprising:
    passing electrical current, having a magnetic field, through an adhesive layer of a cured bondline embedded in the at least one type of aircraft,
    wherein a current sensor network is embedded in the adhesive layer, and wherein the current sensor network comprises at least one current sensor node;
    inducing induced current in the current sensor network in response to the magnetic field;
    sensing, with the at least one current sensor node embedded in the at least one type of aircraft, the induced current;
    generating, with the at least one current sensor node, at least one current signal representative of the induced current;
    determining electromagnetic density data associated with at least one region of the at least one type of aircraft by using the at least one current signal; and
    creating an index that provides a numeric representation for predicted lightning strike damage to the at least one type of aircraft based on the electromagnetic density data, dimensions of the at least one type of aircraft, and design features of the at least one type of aircraft.

2. The method of claim 1, wherein the method further comprises:
    determining the dimensions of the at least one type of aircraft by measuring the dimensions of the at least one type of aircraft; and
    determining the design features of the at least one type of aircraft by assessing the design features of the at least one type of aircraft.

3. The method of claim 1, wherein the index further comprises a numeric representation for predicted lightning strike damage to a specific location on the at least one type of aircraft based on the electromagnetic density data, the dimensions of the at least one type of aircraft, and the design features of the at least one type of aircraft.

4. The method of claim 1, wherein the method further comprises modifying the numeric representation with at least one factor relating to the respective at least one type of aircraft.

5. The method of claim 4, wherein the method further comprises assigning a numeric value to the at least one factor.

6. The method of claim 5, wherein the method further comprises determining an algorithmic association between the numeric representation with the numeric value of the at least one factor.

7. The method of claim 4, wherein the at least one factor comprises a departure frequency of each of the at least one type of aircraft.

8. The method of claim 4, wherein the at least one factor comprises a geographic region in which each of the at least one type of aircraft operates.

9. The method of claim 4, wherein the at least one factor comprises an altitude at which each of the at least one type of aircraft operates.

10. The method of claim 9, wherein the at least one factor further comprises a frequency of a specific altitude within a constant time at which each of the at least one type of aircraft operates.

11. The method of claim 4, wherein the at least one factor comprises a time period during which each of the at least one type of aircraft operates.

12. The method of claim 11, wherein the time period is a specified calendar time period.

13. The method of claim 11, wherein the time period is a seasonal time period.

14. The method of claim 11, wherein the time period is adjustable.

15. The method of claim 4, wherein the method further comprises:
    determining an impact level associated with at least one of: the at least one type of aircraft, the electromagnetic density data, the dimensions of the at least one type of aircraft, the design features of the at least one type of aircraft, and the at least one factor; and
    modifying at least one of the numeric representation and the at least one factor with the associated impact level.

16. The method of claim 15, wherein each impact level is obtained from a table that displays each impact level associated with the respective at least one type of aircraft, the electromagnetic density data, the dimensions of the at least one type of aircraft, the design features of the at least one type of aircraft, and the at least one factor.

17. A system for predicting lightning strike damage to at least one type of aircraft, the system comprising:
    an adhesive layer of a cured bondline, embedded in the at least one type of aircraft, to pass electrical current through,
    wherein the electrical current has a magnetic field;
    a current sensor network embedded in the adhesive layer, wherein the current sensor network comprises at least one current sensor node, and wherein induced current is induced in the current sensor network in response to the magnetic field;
    the at least one current sensor node, embedded in the at least one type of aircraft, to sense the induced current, and to generate at least one current signal representative of the induced current; and
    at least one computer processor to determine electromagnetic density data associated with at least one region of the at least one type of aircraft by using the at least one current signal, and to create an index that provides a numeric representation for predicted lightning strike damage to the at least one type of aircraft based on the electromagnetic density data, dimensions of the at least one type of aircraft, and design features of the at least one type of aircraft.

18. The system of claim 17, wherein the current sensor network further comprises at least one inductive coil.

* * * * *